(12) United States Patent
Hepworth et al.

(10) Patent No.: US 11,253,000 B2
(45) Date of Patent: Feb. 22, 2022

(54) RECEPTACLE SECTION FOR AN AEROSOL PROVISION ARTICLE

(71) Applicant: BRITISH AMERICAN TOBACCO (INVESTMENTS) LIMITED, London (GB)

(72) Inventors: Richard Hepworth, Southampton (GB); Colin Dickens, London (GB)

(73) Assignee: NICOVENTURES TRADING LIMITED, London (GB)

( * ) Notice: Subject to any disclaimer, the term of this patent is extended or adjusted under 35 U.S.C. 154(b) by 253 days.

(21) Appl. No.: 16/333,570

(22) PCT Filed: Sep. 12, 2017

(86) PCT No.: PCT/EP2017/072811
§ 371 (c)(1),
(2) Date: Mar. 14, 2019

(87) PCT Pub. No.: WO2018/050610
PCT Pub. Date: Mar. 22, 2018

(65) Prior Publication Data
US 2019/0254346 A1 Aug. 22, 2019

(30) Foreign Application Priority Data
Sep. 14, 2016 (GB) ...................... 1615601

(51) Int. Cl.
*A24F 13/00* (2006.01)
*A24F 40/30* (2020.01)
(Continued)

(52) U.S. Cl.
CPC .............. *A24F 40/30* (2020.01); *A24F 40/42* (2020.01); *A61M 11/042* (2014.02);
(Continued)

(58) Field of Classification Search
CPC ........................... A24F 47/008; A61M 11/042
(Continued)

(56) References Cited

U.S. PATENT DOCUMENTS 3,894,544 A 7/1975 Egri
4,338,931 A * 7/1982 Cavazza ........... A61M 15/0028
128/203.15

(Continued)

FOREIGN PATENT DOCUMENTS

AR 089648 A1 9/2014
AR 091949 A1 3/2015
(Continued)

OTHER PUBLICATIONS

International Preliminary Report on Patentability, Application No. PCT/EP2017/072811, dated Aug. 20, 2018, 7 pages.
(Continued)

*Primary Examiner* — Neil Abrams
(74) *Attorney, Agent, or Firm* — Patterson Thuente Pedersen, P.A.

(57) ABSTRACT

A receptacle section for an aerosol provision article, arranged for receiving an element for modifying a property of aerosol passing through said element received in the receptacle section in use. The receptacle section having a configuration defining a flow path for said aerosol to flow through the receptacle section. The receptacle section including a first portion and a second portion moveable, the second portion being slidably mounted to the first portion. The receptacle section being arranged to allow at least one of insertion or removal of the element into or from the receptacle section in a direction substantially perpendicular to the longitudinal axis of the receptacle section.

19 Claims, 14 Drawing Sheets

(51) Int. Cl.
*A61M 11/04* (2006.01)
*A61M 15/00* (2006.01)
*A61M 15/06* (2006.01)
*A24F 40/42* (2020.01)
*A24F 40/10* (2020.01)
*A24F 40/20* (2020.01)

(52) U.S. Cl.
CPC ........ *A61M 15/0028* (2013.01); *A61M 15/06* (2013.01); *A24F 40/10* (2020.01); *A24F 40/20* (2020.01); *A61M 2205/3653* (2013.01); *A61M 2205/8206* (2013.01)

(58) Field of Classification Search
USPC .......................................................... 131/329
See application file for complete search history.

(56) References Cited

U.S. PATENT DOCUMENTS

| | | | |
|---|---|---|---|
| 4,714,082 A | 12/1987 | Banerjee et al. | |
| 5,099,861 A | 3/1992 | Clearman et al. | |
| 6,382,465 B1 | 5/2002 | Greiner-Perth | |
| 6,606,992 B1* | 8/2003 | Schuler | A61M 15/0083 128/203.15 |
| 6,705,313 B2 | 3/2004 | Niccolai | |
| 6,708,846 B1 | 3/2004 | Fuchs et al. | |
| 7,726,320 B2* | 6/2010 | Robinson | A24B 15/167 131/200 |
| 8,377,009 B2 | 2/2013 | Sullivan et al. | |
| 8,499,766 B1* | 8/2013 | Newton | A24F 40/40 131/273 |
| 8,997,753 B2 | 4/2015 | Li et al. | |
| 8,997,754 B2 | 4/2015 | Tucker et al. | |
| 9,004,073 B2 | 4/2015 | Tucker et al. | |
| 9,247,773 B2 | 2/2016 | Memari et al. | |
| 9,282,772 B2 | 3/2016 | Tucker et al. | |
| 9,693,587 B2 | 7/2017 | Plojoux et al. | |
| 10,010,687 B2* | 7/2018 | Von Schuckmann | A61M 15/0041 |
| 10,015,990 B2* | 7/2018 | Mironov | A24B 15/16 |
| 10,172,390 B2* | 1/2019 | Nakano | A61M 11/042 |
| 10,368,583 B2* | 8/2019 | Takeuchi | A24F 40/53 |
| 10,426,199 B2 | 10/2019 | Turner et al. | |
| 10,470,491 B2 | 11/2019 | Sutton et al. | |
| 10,492,526 B2 | 12/2019 | Sampson et al. | |
| 10,758,686 B2* | 9/2020 | Reevell | A24F 40/53 |
| 2005/0000518 A1 | 1/2005 | Dunkley et al. | |
| 2005/0016533 A1 | 1/2005 | Schuler | |
| 2005/0022813 A1 | 2/2005 | Alston | |
| 2005/0048003 A1 | 3/2005 | Ohki et al. | |
| 2005/0056280 A1 | 3/2005 | Alston et al. | |
| 2005/0081852 A1 | 4/2005 | Rangachari | |
| 2005/0150492 A1 | 7/2005 | Dunkley et al. | |
| 2007/0012327 A1 | 1/2007 | Karles et al. | |
| 2008/0092912 A1 | 4/2008 | Robinson et al. | |
| 2011/0126848 A1 | 6/2011 | Zuber et al. | |
| 2013/0042865 A1 | 2/2013 | Monsees et al. | |
| 2013/0068081 A1 | 3/2013 | Kronberg et al. | |
| 2013/0192615 A1 | 8/2013 | Tucker et al. | |
| 2013/0192616 A1 | 8/2013 | Tucker et al. | |
| 2013/0192619 A1 | 8/2013 | Tucker et al. | |
| 2013/0192620 A1 | 8/2013 | Tucker et al. | |
| 2013/0192621 A1 | 8/2013 | Li et al. | |
| 2013/0192622 A1 | 8/2013 | Tucker et al. | |
| 2013/0192623 A1 | 8/2013 | Tucker et al. | |
| 2013/0298905 A1 | 11/2013 | Levin et al. | |
| 2013/0312742 A1 | 11/2013 | Monsees et al. | |
| 2014/0202479 A1 | 7/2014 | Nicholls et al. | |
| 2015/0027469 A1 | 1/2015 | Tucker et al. | |
| 2015/0027477 A1 | 1/2015 | Yoshino et al. | |
| 2015/0083150 A1 | 3/2015 | Conner et al. | |
| 2015/0245654 A1 | 9/2015 | Memari et al. | |
| 2015/0245655 A1 | 9/2015 | Memari et al. | |
| 2015/0245656 A1 | 9/2015 | Memari et al. | |
| 2015/0245657 A1 | 9/2015 | Memari et al. | |
| 2015/0245662 A1 | 9/2015 | Memari et al. | |
| 2015/0245663 A1 | 9/2015 | Memari et al. | |
| 2015/0245664 A1 | 9/2015 | Memari et al. | |
| 2015/0245665 A1 | 9/2015 | Memari et al. | |
| 2015/0245666 A1 | 9/2015 | Memari et al. | |
| 2015/0245667 A1 | 9/2015 | Memari et al. | |
| 2015/0245668 A1 | 9/2015 | Memari et al. | |
| 2015/0313281 A1 | 11/2015 | Bonici et al. | |
| 2015/0359266 A1 | 12/2015 | Memari et al. | |
| 2015/0374035 A1 | 12/2015 | Sanchez et al. | |
| 2016/0007648 A1 | 1/2016 | Sutton et al. | |
| 2017/0347706 A1 | 12/2017 | Aoun et al. | |
| 2017/0360088 A1 | 12/2017 | Pijnenburg et al. | |
| 2018/0027882 A1 | 2/2018 | Hepworth et al. | |
| 2018/0279678 A1 | 10/2018 | Hepworth et al. | |
| 2018/0360122 A1 | 12/2018 | Aoun et al. | |
| 2019/0098930 A1* | 4/2019 | Fallon | A24F 40/42 |
| 2019/0125988 A1* | 5/2019 | Trzecieski | A61M 15/06 |
| 2019/0230990 A1 | 8/2019 | Hepworth | |
| 2019/0254343 A1 | 8/2019 | Hepworth et al. | |
| 2019/0254344 A1 | 8/2019 | Hepworth et al. | |
| 2019/0254345 A1 | 8/2019 | Hepworth et al. | |
| 2020/0046026 A1* | 2/2020 | Pijnenburg | H05B 3/06 |
| 2020/0060333 A1 | 2/2020 | Sutton et al. | |
| 2020/0390149 A1* | 12/2020 | Hepworth | A24F 40/10 |

FOREIGN PATENT DOCUMENTS

| | | |
|---|---|---|
| AU | 2013214984 A1 | 8/2014 |
| AU | 2013214987 A1 | 8/2014 |
| AU | 2013214991 A1 | 8/2014 |
| AU | 2013214993 A1 | 8/2014 |
| AU | 2013214994 A1 | 8/2014 |
| AU | 2013214997 A1 | 8/2014 |
| AU | 2013214998 A1 | 8/2014 |
| CA | 2845090 A1 | 2/2013 |
| CA | 2862105 A1 | 8/2013 |
| CA | 2862294 A1 | 8/2013 |
| CA | 2863185 A1 | 8/2013 |
| CA | 2863189 A1 | 8/2013 |
| CA | 2867620 A1 | 8/2013 |
| CA | 2867624 A1 | 8/2013 |
| CA | 2868313 A1 | 8/2013 |
| CN | 2760984 | 3/2006 |
| CN | 104219973 A | 12/2014 |
| CN | 104244749 A | 12/2014 |
| CN | 104244750 A | 12/2014 |
| CN | 104284606 A | 1/2015 |
| CN | 104302197 A | 1/2015 |
| CN | 104394722 A | 3/2015 |
| CN | 204275207 U | 4/2015 |
| CN | 104661544 A | 5/2015 |
| CN | 204560971 | 8/2015 |
| CN | 104968225 A | 10/2015 |
| EA | 201490448 A1 | 12/2014 |
| EP | 1555899 B1 | 12/2006 |
| EP | 2083643 A1 | 8/2009 |
| EP | 2723429 A1 | 4/2014 |
| EP | 2727619 A2 | 5/2014 |
| EP | 2740506 A1 | 6/2014 |
| EP | 2740507 A1 | 6/2014 |
| EP | 2740508 A1 | 6/2014 |
| EP | 2727619 A3 | 7/2014 |
| EP | 2756859 A1 | 7/2014 |
| EP | 2756860 A1 | 7/2014 |
| EP | 2809180 A1 | 12/2014 |
| EP | 2809182 A2 | 12/2014 |
| EP | 2809183 A1 | 12/2014 |
| EP | 2809184 A1 | 12/2014 |
| EP | 2809185 A1 | 12/2014 |
| EP | 2809186 A1 | 12/2014 |
| EP | 2809187 A1 | 12/2014 |
| EP | 2723429 A4 | 4/2015 |
| EP | 2809180 A4 | 7/2015 |
| EP | 2809184 A4 | 7/2015 |
| EP | 2809187 A4 | 7/2015 |
| EP | 2809182 A4 | 8/2015 |
| EP | 2809183 A4 | 8/2015 |

(56) References Cited

FOREIGN PATENT DOCUMENTS

| | | |
|---|---|---|
| EP | 2809185 A4 | 8/2015 |
| EP | 2809186 A4 | 9/2015 |
| EP | 2948006 A1 | 12/2015 |
| EP | 2964038 A1 | 1/2016 |
| EP | 2975956 A1 | 1/2016 |
| EP | 3039972 A1 | 7/2016 |
| GB | 201413018 | 9/2014 |
| GB | 201413019 | 9/2014 |
| GB | 201413021 | 9/2014 |
| GB | 201413025 | 9/2014 |
| GB | 201413027 | 9/2014 |
| GB | 201413028 | 9/2014 |
| GB | 201413030 | 9/2014 |
| GB | 201413032 | 9/2014 |
| GB | 201413034 | 9/2014 |
| GB | 201413036 | 9/2014 |
| GB | 201413037 | 9/2014 |
| GB | 2513061 A | 10/2014 |
| GB | 2523585 A | 9/2015 |
| GB | 2523585 A8 | 9/2015 |
| GB | 2525080 A | 10/2015 |
| GB | 2525294 A | 10/2015 |
| GB | 2525295 A | 10/2015 |
| GB | 2525480 A | 10/2015 |
| GB | 2525722 A | 11/2015 |
| GB | 2525723 A | 11/2015 |
| GB | 2525724 A | 11/2015 |
| GB | 2525725 A | 11/2015 |
| GB | 2525726 A | 11/2015 |
| GB | 2525727 A | 11/2015 |
| GB | 2529919 A | 3/2016 |
| GB | 2531633 A | 4/2016 |
| HK | 1197203 A1 | 1/2015 |
| HK | 1198138 A1 | 3/2015 |
| HK | 1198142 A1 | 3/2015 |
| HK | 1198143 A1 | 3/2015 |
| HK | 1200128 A1 | 7/2015 |
| HK | 1200129 A1 | 7/2015 |
| HK | 1203128 A1 | 10/2015 |
| IL | 233651 | 8/2014 |
| IL | 233896 | 9/2014 |
| IL | 230930 A | 6/2017 |
| IL | 233851 A | 6/2019 |
| IL | 233653 A | 4/2020 |
| IL | 233885 A | 5/2020 |
| IL | 233894 A | 5/2020 |
| IL | 233895 A | 5/2020 |
| JP | S5736898 U | 2/1982 |
| JP | S6033891 U | 3/1985 |
| JP | H022331 | 1/1990 |
| JP | 2006503572 A | 2/2006 |
| JP | 2010506594 A | 3/2010 |
| JP | 2010536336 A | 12/2010 |
| JP | 2012507287 A | 3/2012 |
| JP | 2014524313 A | 9/2014 |
| JP | 2014532433 A | 12/2014 |
| JP | 2015503335 A | 2/2015 |
| JP | 2015505474 A | 2/2015 |
| JP | 2015505475 A | 2/2015 |
| JP | 2015505476 A | 2/2015 |
| JP | 2015506182 A | 3/2015 |
| JP | 2015508641 A | 3/2015 |
| JP | 2015512617 A | 4/2015 |
| JP | 2015513393 A | 5/2015 |
| JP | 2015518730 A | 7/2015 |
| JP | 2015536154 A | 12/2015 |
| JP | 2016509852 A | 4/2016 |
| JP | 2016517701 A | 6/2016 |
| KR | 20140070543 A | 6/2014 |
| KR | 20140090138 A | 7/2014 |
| KR | 20140125822 A | 10/2014 |
| KR | 20140125827 A | 10/2014 |
| KR | 20140125828 A | 10/2014 |
| KR | 20140125829 A | 10/2014 |
| KR | 20140127288 A | 11/2014 |
| KR | 20150003845 A | 1/2015 |
| KR | 20150005514 A | 1/2015 |
| KR | 20150035488 A | 4/2015 |
| MA | 20150054 A1 | 2/2015 |
| MA | 20150055 A1 | 2/2015 |
| MA | 20150056 A1 | 2/2015 |
| MA | 20150057 A1 | 2/2015 |
| MA | 20150058 A1 | 2/2015 |
| MA | 20150153 A1 | 5/2015 |
| MA | 20150169 A1 | 6/2015 |
| MX | 2014009396 A | 2/2015 |
| MX | 2014009398 A | 2/2015 |
| MX | 2014009393 A | 5/2015 |
| MX | 2014009394 A | 5/2015 |
| MX | 2014009397 A | 5/2015 |
| NZ | 627439 A | 9/2015 |
| NZ | 628058 A | 1/2016 |
| RU | 157882 U1 | 12/2015 |
| RU | 2581999 C2 | 4/2016 |
| SG | 2014013627 A | 7/2014 |
| TW | 201315397 A | 4/2013 |
| WO | WO-2010045671 A1 | 4/2010 |
| WO | WO-2012156695 A1 | 11/2012 |
| WO | WO-2013020280 A1 | 2/2013 |
| WO | WO-2013025921 A1 | 2/2013 |
| WO | WO-2013068081 A1 | 5/2013 |
| WO | WO-2013068100 A1 | 5/2013 |
| WO | WO-2013098405 A2 | 7/2013 |
| WO | WO-2013116558 A1 | 8/2013 |
| WO | WO-2013116561 A1 | 8/2013 |
| WO | WO-2013116565 A1 | 8/2013 |
| WO | WO-2013116567 A1 | 8/2013 |
| WO | WO-2013116568 A2 | 8/2013 |
| WO | WO-2013116571 A1 | 8/2013 |
| WO | WO-2013116572 A1 | 8/2013 |
| WO | WO-2013120566 A2 | 8/2013 |
| WO | WO-2013121608 A1 | 8/2013 |
| WO | WO-2013138384 A2 | 9/2013 |
| WO | WO-2013138384 A3 | 10/2013 |
| WO | WO-2013179524 A1 | 12/2013 |
| WO | WO-2014116974 A1 | 7/2014 |
| WO | WO-2014140273 A2 | 9/2014 |
| WO | WO 2013156339 | 10/2014 |
| WO | WO-2014158051 A1 | 10/2014 |
| WO | WO-2014159250 A1 | 10/2014 |
| WO | WO-2013116568 A3 | 11/2014 |
| WO | WO-2014184239 A1 | 11/2014 |
| WO | WO-2015013108 A2 | 1/2015 |
| WO | WO-2015013108 A3 | 4/2015 |
| WO | WO-2015047954 A1 | 4/2015 |
| WO | WO-2015128665 A1 | 9/2015 |
| WO | WO-2015128666 A1 | 9/2015 |
| WO | WO-2015128667 A1 | 9/2015 |
| WO | WO-2016024083 A1 | 2/2016 |
| WO | WO 2016076178 | 5/2016 |
| WO | WO-2016135342 A2 | 9/2016 |
| WO | WO-2017149152 A1 | 9/2017 |
| WO | WO-2017160559 A1 | 9/2017 |

OTHER PUBLICATIONS

International Search Report, Application No. PCT/EP2017/072811, dated Dec. 11, 2017, 4 pages.
Application and File History for U.S. Appl. No. 16/333,570, filed Mar. 24, 2019, Inventor: Hepworth et al.
Application and File History for U.S. Appl. No. 16/333,567, filed Mar. 24, 2019, Inventor: Hepworth et al.
Application and File History for U.S. Appl. No. 16/333,568, filed Mar. 24, 2019, Inventor: Hepworth et al.
Communication pursuant to Article 94(3) EPC for Application No. 1778008.3, dated Sep. 11, 2020, 8 pages.
International Preliminary Report on Patentability for Application No. PCT/EP2017/073057, dated Mar. 28, 2019, 9 pages.
International Preliminary Report on Patentability for Application No. PCT/EP2017/072814, dated Nov. 30, 2018, 8 pages.
International Preliminary Report on Patentability for Application No. PCT/EP2017/072813, dated Nov. 30, 2018, 9 pages.

(56) References Cited

OTHER PUBLICATIONS

International Preliminary Report on Patentability for Application No. PCT/EP2017/073061, dated Mar. 28, 2019, 7 pages.
International Search Report and Written Opinion for Application No. PCT/EP2017/072813, dated Dec. 11, 2017, 12 pages.
International Search Report and Written Opinion for Application No. PCT/EP2017/072814, dated Dec. 11, 2017, 12 pages.
International Search Report and Written Opinion for Application No. PCT/EP2017/073057, dated Feb. 7, 2018, 16 pages.
International Search Report and Written Opinion for Application No. PCT/EP2017/073061, dated Jan. 8, 2018, 13 pages.
Korean Office Action dated Oct. 26, 2020 for Korean Application No. 10-2019-7010642 27 pages.
Korean Office Action dated Oct. 26, 2020 for Korean Application No. 10-2019-7010644, 21 pages.
Notice of Reasons for Rejection for Japanese Application No. 2019-535975, dated Jul. 7, 2020, 9 pages.
Office Action For Korean Application No. 10-2019-7010649, dated Jan. 19, 2021, 7 pages.
Office Action dated Feb. 2, 2021 for Japanese Application No. JP2019-513828, 7 pages.
Office Action dated Aug. 20, 2020 for Russian Application No. 2019107330, 13 pages.
Office Action dated Jul. 21, 2020 for European Application No. 17780009.1, 7 pages.
Office Action dated Jul. 21, 2020 for Japanese Application No. 2019-513761, 11 pages.
Office Action dated Jul. 21, 2020 for Japanese Application No. 2019-513827, 9 pages.
Office Action dated Jul. 21, 2020 for Japanese Application No. 2019-513842, 11 pages.
Office Action dated Jul. 7, 2020 for Japanese Application No. JP2019-513828, 12 pages.
Search Report dated Mar. 2, 2018 for Great Britain Application No. GB1615609.3, 4 pages.
U.S. Appl. No. 16/333,563, filed Mar. 14, 2019, inventors Hepworth, et al.

* cited by examiner

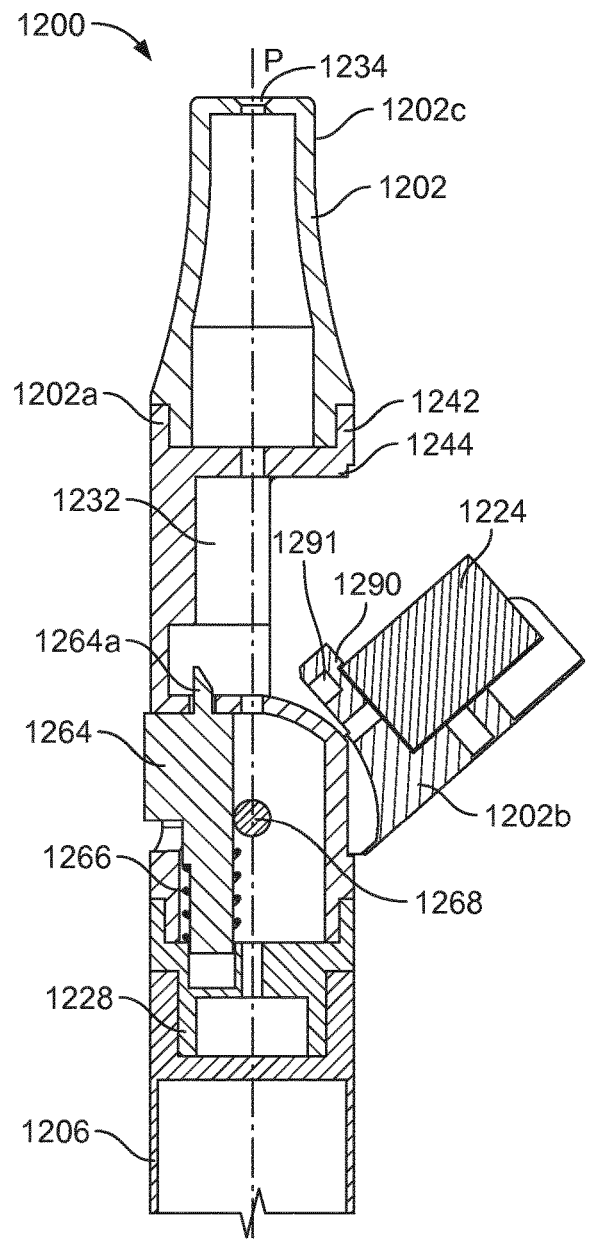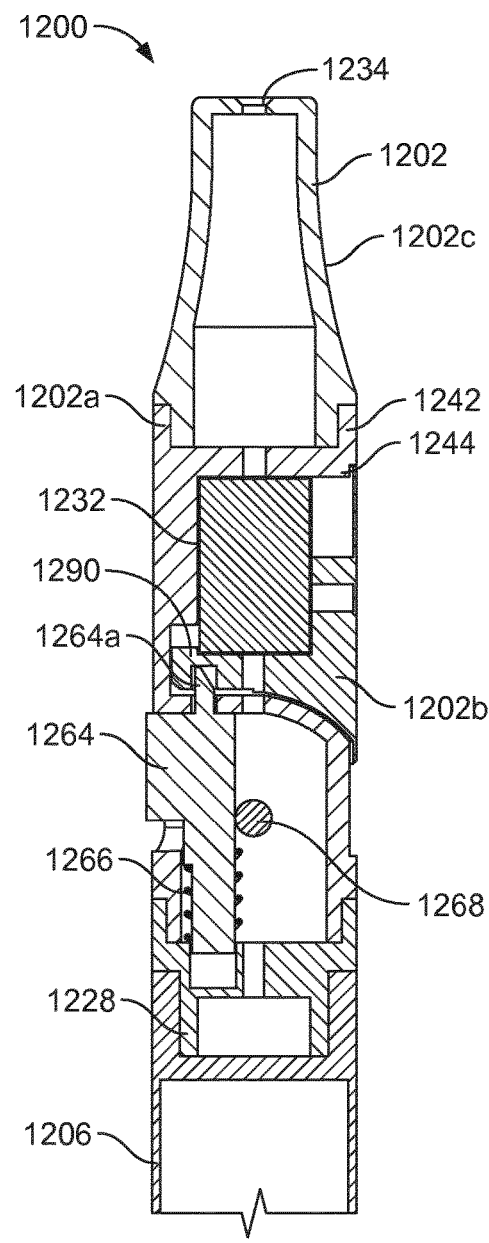

RECEPTACLE SECTION FOR AN AEROSOL PROVISION ARTICLE

PRIORITY CLAIM

The present application is a National Phase entry of PCT Application No. PCT/EP2017/072811, filed Sep. 12, 2017, which claims priority from GB Patent Application No. 1615601.0, filed Sep. 14, 2016, which is hereby fully incorporated herein by reference.

TECHNICAL FIELD

The present disclosure relates to a receptacle section, and more particularly to a receptacle section for an aerosol provision article.

BACKGROUND

Smoking articles such as cigarettes, cigars and the like burn tobacco during use to create tobacco smoke. Attempts have been made to provide alternatives to these articles that burn tobacco by creating products that release compounds without burning.

Examples of such products are heating devices which release compounds by heating, but not burning, the material. The material may be for example tobacco or other non-tobacco products, which may or may not contain nicotine. As another example, there are aerosol provision articles such as so-called e-cigarette devices. These devices typically contain a liquid which is heated to vaporize the liquid to produce an inhalable vapor or aerosol. The liquid may contain nicotine and/or flavorings and/or aerosol-generating substances, such as glycerol. The known e-cigarette devices typically do not contain flavorings other than those in the liquid.

SUMMARY

According to a first aspect of the present disclosure, there is provided a receptacle section for an aerosol provision article, the aerosol provision article for generating a flow of aerosol in use, the receptacle section arranged for receiving therein an element for modifying a property of aerosol passing through said element received in the receptacle section in use, the receptacle section being configurable between a first configuration and a different, second configuration, the first configuration defining a flow path for said aerosol to flow through the receptacle section via said element received in the receptacle section in use, and the second configuration allowing said element to be inserted into and/or removed from the receptacle section.

The receptacle section may comprise a first portion and a second portion moveable relative to the first portion, and a movement of the second portion relative to the first portion may change the configuration of the receptacle section between the first configuration and the second configuration.

The movement may comprise movement substantially parallel to a longitudinal axis of the receptacle section.

The second portion may be slidably mounted to the first portion thereby to allow sliding of the second portion relative to the first portion, parallel to the longitudinal axis of the receptacle section, between the first configuration and the second configuration.

The receptacle section may be arranged to allow, when in the second configuration, insertion and/or removal of said element into and/or from the receptacle section in a direction substantially parallel to the longitudinal axis of the receptacle section.

The receptacle section may be arranged to allow the insertion and/or removal of said element through an opening of the second portion, the opening being for outlet of said aerosol flowing through the receptacle section in use for inhalation by a user.

The receptacle section may comprise, at the opening, a lip portion for retaining said element in the receptacle section in use.

Movement of the second portion towards the first portion may cause said element when inserted in the receptacle section to protrude out of the opening.

The receptacle section may comprise, at the opening, a or the lip portion, and the lip portion may be arranged to cause said element to remain protruded out of the opening on a subsequent movement of the second portion away from the first portion.

The receptacle section may be biased to the first configuration.

The second portion may comprise a housing, and the first portion may comprise a plurality of resilient members, the resilient members defining between them a receiving region for receiving said element in use, and in the first configuration the resilient members may be received in the housing and define between them a first radial dimension of the receiving region for retaining said element in the receiving section in use, and in the second configuration the resilient members may each protrude out of the housing and define between them a second, larger radial dimension of the receiving region for allowing said element to be inserted into and/or removed from the receptacle section.

The receptacle section may be arranged to allow insertion and/or removal of said element into and/or from the receptacle section in a direction substantially perpendicular to the longitudinal axis of the receptacle section.

The second portion may be receivable in the first portion, and a side wall of the second portion may define an opening, wherein in the second configuration the opening may be exposed for insertion and/or removal of said element into the second portion through the opening, and wherein in the first configuration the opening may be closed off by the first portion.

The receptacle section may comprise a third portion for closing off the opening, the third portion being pivotally mounted to the second portion, thereby to allow pivoting of the third portion relative to the second portion, and in the second configuration the third portion may be exposed out of the first portion thereby to allow said pivoting of the third portion, and in the first configuration the third portion may be received in the first portion.

The first portion may be receivable in the second portion, and a side wall of the first portion may define an opening, and in the second configuration the opening may be exposed for insertion and/or removal of said element into the first portion through the opening, and in the closed configuration the opening may be closed off by the second portion.

The first portion may comprise a retaining element to releasably retain the second portion relative to the first portion such that the receptacle section is in the first configuration.

The receptacle section may be biased towards the second configuration.

The second portion may be removable from the first portion, and the receptacle section may be in the second configuration when the second portion is removed from the first portion, and the receptacle section may be in the first configuration when the second portion is connected to the first portion.

The first portion may comprise a receiving portion for allowing, when the second portion is removed, insertion and/or removal of said element into and/or from the receiving portion in a direction substantially parallel to the longitudinal axis of the receptacle section.

The receiving portion may be arranged such that said element received in the receiving portion in use protrudes out from the receiving portion.

The receiving portion may comprise a plurality of resilient members extending in a direction substantially parallel to the longitudinal axis of the receptacle section, and the resilient members may define between them a receiving region for receiving said element.

The second portion may comprise a receiving portion for allowing, when the second portion is removed, insertion and/or removal of said element into and/or from the receiving portion in a direction substantially perpendicular to the longitudinal axis of the receptacle section.

The receiving portion may be receivable in the first portion.

The receiving portion may define an aperture into which said element can be inserted to be supported by the receiving portion.

The first portion may comprise a receiving portion for allowing, when the second portion is removed, insertion and/or removal of said element into and/or from the receiving portion in a direction substantially perpendicular to the longitudinal axis of the receptacle section.

At least a portion of the second portion may be for receipt into a user's mouth.

The movement may comprise rotation about a longitudinal axis of the receptacle section.

The second portion may be rotationally mounted with respect to the first portion, thereby to allow the second portion to rotate relative to the first portion, between the first configuration and the second configuration.

The first portion may define an opening and the second portion may define an opening, and in the second configuration the opening of the first portion and the opening of the second portion may be aligned with respect to one another to allow insertion and/or removal of said element into and/or from the receptacle section, through the opening of the first portion and the opening of the second portion, and in the first configuration, the opening of the first portion and the opening of the second portion may be misaligned with respect to one another.

The second portion may be received in the first portion, and the opening of the first portion may be in a side wall of the first portion, and the opening of the second portion may be in a side wall of the second portion, such that in the second configuration the opening of the first portion and the opening of the second portion are aligned with respect to one another to allow insertion and/or removal of said element into and/or from the first portion, through the opening of the first portion and the opening of the second portion, and such that in the first configuration the side wall of the second portion closes off the opening of the first portion.

The movement may comprise rotation about an axis substantially perpendicular to a longitudinal axis of the receptacle.

The second portion may be pivotally mounted to the first portion, thereby to allow pivoting of the second portion relative to the first portion, about an axis substantially perpendicular to the longitudinal axis of the receptacle, between the first configuration and the second configuration.

A side wall of the first portion may define an opening that may allow, in the second configuration, insertion and/or removal of said element into and/or from the receptacle section, through the opening, in a direction substantially perpendicular to the longitudinal axis of the receptacle section, and in the first configuration the second portion may close off the opening.

The first portion may comprise a retaining element to releasably retain the second portion relative to the first portion such that the receptacle section is in the first configuration.

The retaining element may comprise a latch to latch the second portion relative to the first portion, and the latch may be operable by a user to release the second portion such that the receptacle section is in the second configuration.

The first portion may define an opening that may allow, in the open configuration, insertion and/or removal of said element into and/or from the first portion, through the opening, in a direction substantially parallel to the longitudinal axis of the receptacle section.

The first portion may be arranged such that said element received in the opening in use protrudes out from the opening.

The first portion may comprise a retaining element to releasably retain the second portion relative to the first portion such that the receptacle section is retained in the first configuration.

The retaining element may be slidable, by a user, in use, along the longitudinal axis of the receptacle between a first position for obstructing said pivoting of the second portion about the first portion, and a second position for allowing said pivoting of the second portion about the first portion.

An interface between the retaining element and the second portion may be angled with respect to a plane parallel to the longitudinal axis of the receptacle, and may be angled with respect to a plane perpendicular to the longitudinal axis of the receptacle.

The retaining element may be biased to the first position.

At least a portion of the second portion may be for receipt into a user's mouth in use.

The receptacle section may have the element received therein.

The property of the aerosol may be one or more of an organoleptic property of the aerosol, a flavor of the aerosol, and the pH of the aerosol.

The element may be self-supporting and/or may be or comprise tobacco and/or may comprise a crushable flavor capsule for releasing, when crushed, a flavorant into said flow of aerosol.

The first portion may comprise a connecting portion for releasably connecting the receptacle section to said aerosol provision article.

According to a second aspect of the present disclosure, there is provided a mouthpiece for an aerosol provision article, said aerosol provision article being for generating a flow of aerosol in use, the mouthpiece comprising the receptacle section according to the first aspect.

According to a third aspect of the present disclosure, there is provided an aerosol provision article for generating a flow of aerosol in use, the aerosol provision article comprising the receptacle section according to the first aspect, and/or the mouthpiece according to the second aspect.

The aerosol provision article may comprise: a container for holding a liquid or a material; a heater for volatilizing liquid held in the container to generate said flow of aerosol in use or for heating but not combusting the material to generate said flow of aerosol in use.

Further features and advantages of the disclosure will become apparent from the following description of embodiments, given by way of example only, which is made with reference to the accompanying drawings.

BRIEF DESCRIPTION OF THE DRAWINGS

FIGS. 12a and 12b show schematic cross sections of a part of an aerosol provision article comprising an eleventh receptacle section in different configurations according to an eleventh example.

DETAILED DESCRIPTION

Figure 1:
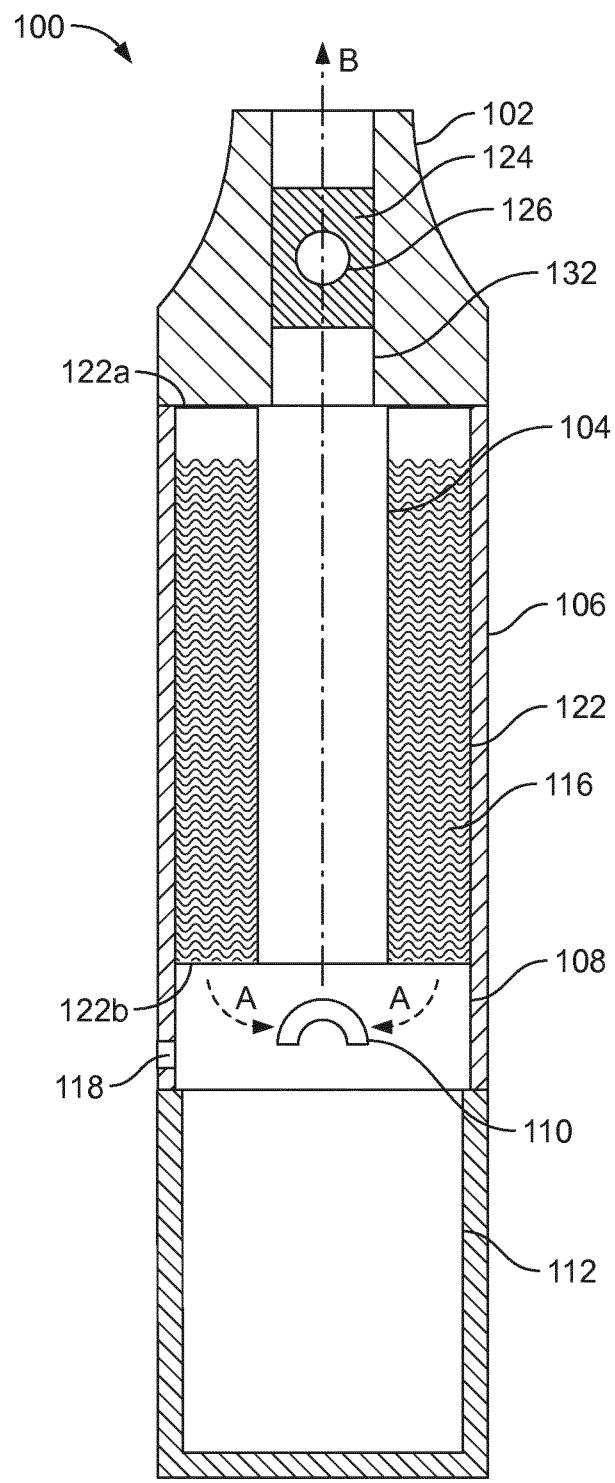
FIG. 1 shows a schematic cross section of an aerosol provision article according to an example.

Referring to FIG. 1, a schematic of an example aerosol provision article 100 is illustrated. The aerosol provision article 100 is an inhalation device (i.e. a user uses it to inhale an aerosol provided by the device). The aerosol provision article is hand-held. In this example, the article 100 is an electronic cigarette device 100. In broad outline, the device 100 volatilizes a liquid to form a vapor or an aerosol which passes through an element 124 received in a mouthpiece 102 of the device 100. The element 124 modifies a property of the vapor or aerosol passing through the mouthpiece 102 for inhalation by a user. For example, the element 124 may be a flavor element 124 for modifying (imparting) a flavor of (to) vapor or aerosol passing there through.

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A colloid is a substance in which microscopically dispersed insoluble particles are suspended throughout another substance.

Returning to FIG. 1, the device 100 comprises an outer body 106 housing a liquid container 122 containing liquid 116, an atomizer 108, and a battery portion 112. The atomizer 108 is (electrically) connected to the battery portion 112.

The mouthpiece 102 is, in this example, removably connected to the outer body 106. The mouthpiece 102 may be removed from the outer body 106, for example to allow access to the liquid container 122, for example to refill the liquid 116 held in the liquid container 122. The mouthpiece 102 has a channel 132 running there through that defines a flow path for a flow of vapor or aerosol. The mouthpiece 102 has removably received in the channel 132 a flavor element 124 for imparting a flavor to said flow of aerosol or vapor that passes through the mouthpiece 102 in use. The flavor element 124 may be or comprise for example tobacco, or other flavored materials that may be used to create a desired taste or aroma, or other properties, such as nicotine content.

The device 100 is arranged so that, in use, as the liquid 116 is volatilized so as to produce an aerosol of liquid droplets or sufficiently heated to produce a vapor, at least some or all or substantially all of the aerosol or vapor passes through the flavor element 124 received in the mouthpiece 102 for example so as to entrain constituents of the flavor element 134 therein. In some examples, a vapor is produced that then at least partly condenses to form on aerosol before exiting the device 100.

The liquid container 122 is provided generally centrally of the outer body 106. The liquid container 122 is annular in shape and defines a channel 104 running through the length of the liquid container 122. The liquid container 122 may be formed of rigid, watertight and airtight materials, such as metal, suitable plastics, etc. It will be appreciated that the liquid container 122 may have a different shape, such as conical, frustoconical, or combination of these, etc.

The atomizer 108 is provided with a heater 110 and a wick (not shown) in (thermal) contact with the heater 110. The orientation of the heater 110 is shown schematically and for example the heater 110 may be a coil having its longitudinal axis perpendicular or parallel to the longitudinal axis of the liquid container 108. The wick (not shown) is in contact with the liquid 116. This may be achieved by for example by the wick (not shown) being inserted through a through hole (not shown) in an end wall 122b of the liquid container 122. Alternatively or additionally, the end wall 122b may be a porous member which allows liquid to pass through from the liquid container 122, and the wick (not shown) may be in contact with the porous end wall 122b. The end wall 122b may be for example in the form of a porous ceramic disk. A porous end wall 122b of this type helps to regulate the flow of liquid onto the wick (not shown). The wick (not shown) is generally absorbent and acts to draw in liquid 116 from the liquid container 122 by capillary action (shown in FIG. 1 by arrows A). The wick can be non-woven and may be for example a cotton or wool material or the like, or a synthetic material, including for example polyester, nylon, viscose, polypropylene or the like, or a ceramic material.

The atomizer 108 is (electrically) connected to a battery in the battery portion 116 to enable the heater 110 to be powered. When the heater 110 is powered (which may be instigated for example by the user operating a button (not shown) of the device 100 or by a puff detector (not shown) of the overall device 100, as is known per se, liquid 116 is drawn (shown in FIG. 1 by arrows A) in from the liquid container 122 by the wick and is heated by the heater 110 to volatilize or vaporize the liquid, so as to generate at least one of a vapor and an aerosol. As the user draws on the mouthpiece 102, air is drawn through an air inlet 118. The liquid 116 is volatized or vaporized by the heater 110 into air from the air inlet 118 thereby to produce a flow of one of a vapor and an aerosol. The flow vapor or aerosol is drawn through the channel 104 of the liquid container 122, into the channel 132 of the mouthpiece 102, through the flavor element 124 received in the mouthpiece 102, and out from the device 100 for inhalation by a user (shown by arrow B in FIG. 1). The vapor or aerosol picks up (entrains) flavor (and/or other constituents) from the flavor element 124. One or more constituents of the flavor element is thereby mixed with the flow of at least one of a vapor and an aerosol. In examples where the flavor element 124 contains or includes nicotine, the vapor or aerosol may thereby also contain nicotine entrained from that solid material. A one way valve (not shown) may be provided, for example at or near an upper end 122a of the liquid container 122, so that the vapor or aerosol can only exit the channel 104 and cannot backflow to the heater 110 or the electronics (not shown) of the device 100.

The flavor element 124 may be or comprise material that may be used to impart a flavor (and/or one or more other constituents) to the aerosol or vapor. In some examples, the one or more constituents of the flavor element may comprise constituents inherent to the material itself. The material may for example consist of or comprise tobacco. As the aerosol or vapor passes through and over the tobacco, the aerosol or vapor entrains organic and other compounds or constituents from the tobacco that lend tobacco its organoleptic properties, thus imparting the flavor to the aerosol or vapor. It will be understood however that materials other than tobacco may be used to impart different flavors (and/or one or more other constituents) to the aerosol or vapor flow. The flavor element 124 may comprise constituents added to a material of the flavor element 124.

Nicotine may be provided in the liquid 116. Accordingly, where it is intended that the device 100 provides nicotine for the user, the nicotine may be provided in the liquid 116, may be obtained from the flavor element 124, or any combination of these. Likewise, flavorings may be added to the flavor element 124 (whether or not the flavor element 124 is or includes tobacco) and/or to the liquid 116. A material of the flavor element 124 may be a solid material, or be a mixture of solid materials, one or more of each comprising one or more constituents that can be mixed with the flow of vapor or aerosol. It will be appreciated that the flavor element 124 may comprise one or more other constituents that are not entrained into the aerosol or vapor passing there through. It will also be appreciated that the flavor element 124 may comprise a portion that does not impart any flavor and/or release any constituents into the flow of a vapor or an aerosol.

The flavor element 124 may be porous, for example so as allow vapor or aerosol to pass through it. The flavor element 124 may be self-supporting, so as to be easily handled by a user (for example easily inserted and/or removed from the mouthpiece 102). For example the flavor element 124 may comprise material wrapped partially or wholly in a wrapper, and/or the flavor element 124 may be supported in a resilient housing, for example a plastic housing (not shown). The flavor element may comprise, for example, a flavored carrier material, such as cellulose acetate or the like. The flavor element 124 may be cylindrical, and/or comprise a cylindrical portion, so as to fit easily and/or tightly into a corresponding cylindrical channel 132 of the mouthpiece 102.

In some examples, the flavor element 124 comprises a crushable flavor capsule 126 for releasing, when crushed for example by a user, a liquid or a gel that flavors a flow of at least one of a vapor and an aerosol. For example, the flavor element 124 may comprise a crushable flavor capsule 126 wrapped or embedded in a suitable carrier material, for example cellulose acetate. The carrier material may comprise a material that allows vapor or aerosol to pass there through. The carrier material may comprise a material that holds the liquid and/or gel released from the crushable flavor capsule 126 when it is crushed. When the capsule 126 is crushed, the liquid or gel contained therein is released into the material so as to flavor vapor or aerosol passing there through.

Various receptacle sections for an aerosol provision article (e.g. device 100 in FIG. 1) will now be described. In broad overview, the various receptacle sections are arranged for receiving therein a flavor element for imparting a flavor to at least one of a vapor and an aerosol passing through said flavor element received in the receptacle section in use. The receptacle sections are configurable between a first configuration and a different, second configuration. The first configuration defines a flow path for the at least one of a vapor and an aerosol to flow through the receptacle section via said flavor element received in the receptacle section in use, whereas the second configuration allows the flavor element to be inserted into and/or removed from the receptacle section. The various receptacle sections therefore provide a convenient way for a user to insert/and or remove a flavor element from an overall aerosol provision article (e.g. device 100 in FIG. 1) in/with which the receptacle section is being used. A user may wish to remove and/or insert a flavor element for example, when the flavor of the flavor element deteriorates, or when a user wishes to change the taste, aroma, or other properties of the vapor or aerosol produced.

For reasons of convenience, as used herein the term aerosol should be taken as encompassing an aerosol, a vapor or a mixture of an aerosol and vapor.

Turning first to FIGS. 2a to 2d, there is illustrated schematically cross sections of part of a device 200 that comprises an example receptacle section 202 in different configurations. In this example, the receptacle section 202 is a mouth-end section 202 of the device 200, that is, the receptacle section 202 is towards an end of the device 200 for receipt into a user's mouth in use. It will be appreciated that in some examples, the receptacle section 202 (or at least a portion thereof) is for receipt into a user's mouth in use, and hence is itself a mouthpiece 202. For brevity, features in FIG. 2 and the functioning thereof that are the same or similar to those features already described with reference to FIG. 1 are given similar reference numerals to as in FIG. 1 but increased by 100, and will not be described in detail again.

The mouth-end section 202 has a first portion 202a and a second portion 202b moveable relative to the first portion 202a. The first portion 202a is received in the second portion 202a. The first portion 202a is removably connected to a body 206 of the overall device 200, via a connecting means 228. The connecting means 228 may be, for example, a threaded connection or the like, for example the first portion 202a may have a male thread connectable to a corresponding female thread of the body 206. The second portion 202b is for receipt into a user's mouth (not shown).

The first portion 202a defines a channel 204 internal thereof, and the second portion 202b defines a channel 232 internal thereof. The first portion 202a (and a portion of the channel 204 thereof) is partially received in the channel 232 of the second portion 202b. The first portion 202a and the second portion 202b are arranged such that the channels 204, 232, in combination, extend from an aerosol outlet 207 of the body 206 of the overall device 200 to an opening 234 of the second portion 202a for outlet of the aerosol for inhalation by a user. The channels 204, 232 thereby define, in combination, a flow path for the aerosol to flow from the outlet 207 of the body 206 of the overall device 200 to the opening 234 of the second portion 202a for inhalation by a user.

Figure 2A:
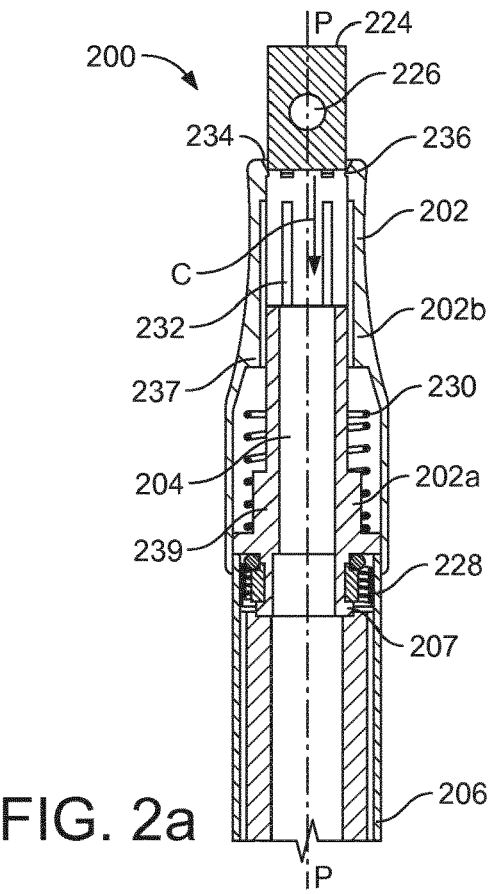
FIGS. 2a to 2d show schematic cross sections of a part of an aerosol provision article comprising a first receptacle section in different configurations according to a first example.
Figure 2B:
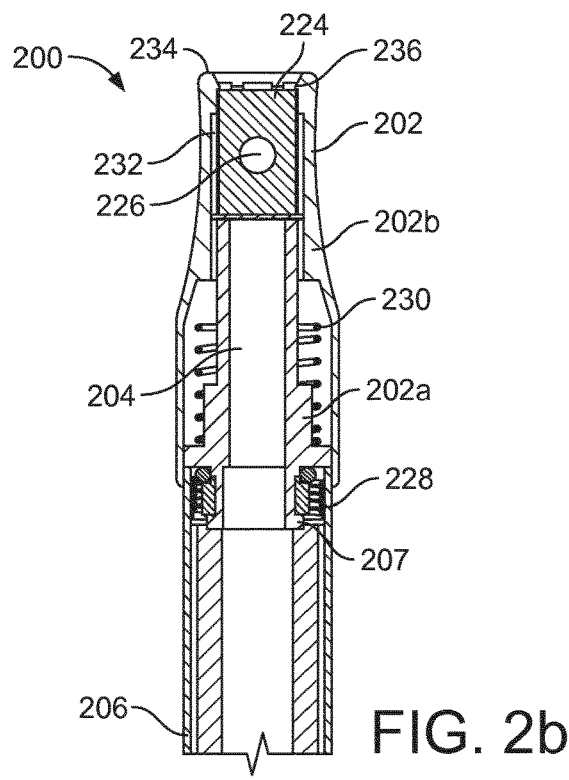
Figure 2C:
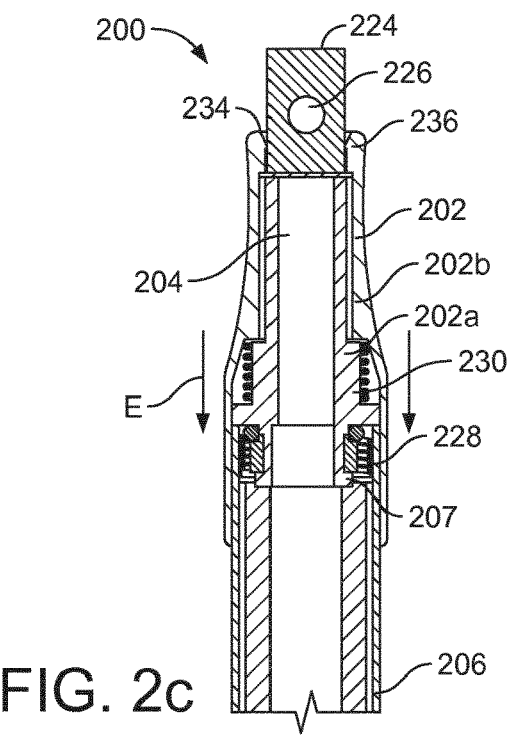
Figure 2D:
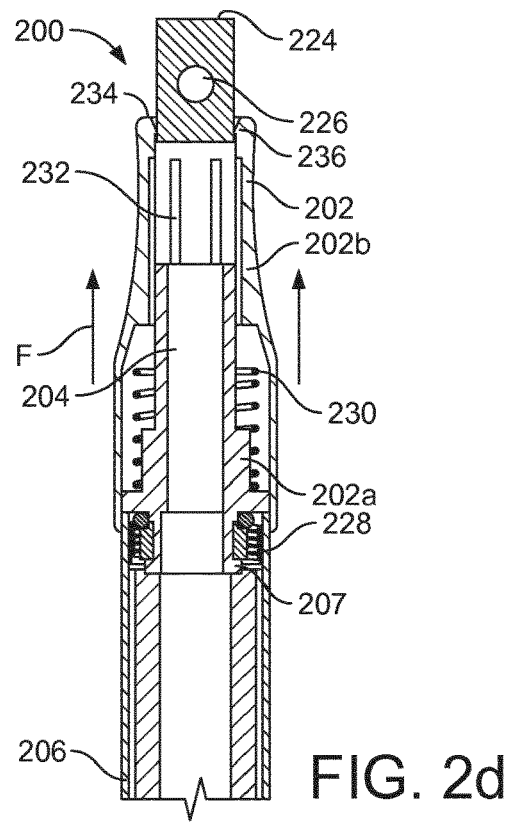

The second portion 202b is slidably mounted to the first portion 202a to enable sliding movement of the second portion 202b relative to the first portion 202a (and hence relative to the body 206 of the overall device 200) substantially parallel to a longitudinal axis P-P of the mouth-end section 202. Movement of the second portion 202b relative to the first portion 202a substantially parallel to the longitudinal axis P-P of the mouth-end section 200 changes the configuration of the mouth-end section 202 between a first (closed) configuration (as shown in FIG. 2c) and an second (open) configuration (as shown in FIG. 2a, FIG. 2b, and FIG. 2d). The mouth-end section 202 is arranged to allow, when in the second configuration, insertion and/or removal of a flavor element 224 into and/or from the mouth-end section 200 in a direction substantially parallel to the longitudinal axis P-P of the mouth-end section 200. In this example, the flavor element 224 can be inserted and/or removed from the channel 232 of the mouth-end section 202 via the opening 234 defined by the second portion 202b.

Specifically, movement of the second portion 202b relative to the first portion 202a changes the extent to which the first portion 202a extends in the channel 232 of the second portion 202b. When the mouth-end section 202 is in the open configuration, the first portion 202a extends a relatively small amount into the channel 232 of the second portion 202a (i.e. the second portion 202a is positioned relatively away from the first portion 202b), such that the remaining (free) length of the channel 232 defined by the second portion 202a is long enough to enable a flavor element 224 be fully received therein (see FIG. 2b in particular). When the mouth-end section 202 is in the closed configuration, the first portion 202a extends a relatively large amount into the channel 232 of the second portion 202a (i.e. the second portion 202b is position relatively towards the first portion 202a), such that the remaining (free) length of the channel 232 defined by the second portion is short enough so that a flavor element 224 is not fully receivable therein, and is instead forced to be exposed (protruding) out of the opening 234 of the second portion 202b (see FIG. 2c). The flavor element 234 being exposed (protruding) out of the opening 234 allows the flavor element 234 to be easily grasped (manipulated) by a user, and hence provides for convenient removal, replacement, and/or insertion of the or another flavor element 234 into the mouth-end section 202.

The mouth-end section 202 comprises a biasing means 230, such as a spring 230, which, in this example, is arranged in an annular space between a part of the first portion 202a and a part of the second portion 202b, and which biases the second portion 202b away from the first portion 202a, and hence biases the mouth-end section 202 to the closed configuration. The mouth-end section comprises a stop (not shown) to prevent the second portion 202b from sliding entirely off the first portion 202a.

The second portion 202b comprises a first lip portion 236, at the opening 234, for retaining the flavor element 224 in the channel 232. The first lip portion 236 protrudes radially inwardly to the channel 236 around the circumference of the opening 236. The first lip portion 236 provides some resistance to the flavor element exiting the channel 232 of the second portion 202b into which it is received. This resistance can be overcome when a user manipulates the mouth-end section 200 to the closed configuration, hence forcing the flavor element 224 to become exposed (protrude) out of the opening 234 of the second portion 202b.

As best seen in FIG. 2c, the first lip portion 236 abuts or opposes a rim of the top of the first portion 202a when the mouth-end section 202 is in the closed configuration. Furthermore, the second portion 202b further comprises a second lip portion 237 that is defined by an internal surface of the second portion 202b about half way along its length and which abuts a third lip portion 239 defined by an external surface of the first portion 202a when the mouth-end section 202 is in the closed configuration.

Describing now the sequence illustrated in FIGS. 2a to 2d, in FIG. 2a, a user (not shown) brings a flavor element 224 (which may comprise, for example, an already crushed crushable flavor capsule 226) to the opening 234 of the second portion 202b, and pushes (arrow C) the flavor element 224 into the channel 232 of the second portion 202b so that it is fully received into the channel 232 of the second portion 202b (as shown in FIG. 2b). As seen in FIG. 2b, the flavor element 224 is retained in the channel 232 by, at one end, the first portion 202a received in the channel 232 of the second portion 202b, and at the other end by the first lip portion 236.

A user may wish to remove the flavor element 224 at some later point in time, for example, when the flavor element 224 has been exhausted of flavor. The user therefore pushes, or pulls, or otherwise manipulates (see arrows E in FIG. 2c) the second portion 202b towards the first portion 202a. This causes the first portion 202a to extend further into the channel 232 of the second portion 202b, which in turn pushes the flavor element 224 partially out of the opening 234 of the second portion 202b (as shown in FIG. 2c). This also causes the spring 230 to become compressed (as shown in FIG. 2c).

When the user ceases to push or pull or otherwise manipulate the second portion 202b, the spring 230 causes the second portion 202b to return to the open configuration (see FIG. 2d). The first lip portion 236 holds the flavor element 224 partially exposed out of the opening 234, i.e. causes the flavor element 224 to remain protruded out of the opening on the subsequent movement of the second portion 202b away from the first portion 202a. The flavor element 224 is therefore presented to a user so that the user can easily and controllably remove the flavor element 224 from the mouth-end section 202.

In use, when the mouth-end section 202 is connected to the rest of the device (e.g. as shown schematically for device 100 in FIG. 1), and when the mouth-end section 202 has a flavor element 224 received therein, and when the mouth-end section 202 is in the closed configuration, when a user draws on the mouth-end section 202, air is drawn in through an air inlet (120 in FIG. 1). A heater (110 in FIG. 1) volatizes liquid (116 in FIG. 1) held in the liquid container (122 in FIG. 1) into the inlet air to generate a flow of aerosol. The flow passes through the channel (104 in FIG. 1) in the liquid container (122 in FIG. 1), through the channel 204 of the first portion 202a, into the channel 232 of the second portion 202b, through the flavor flavour element 234, and exits from the outlet 234 of the second portion 202b for inhalation by the user. The flow of an aerosol through the flavor element 224 thereby entrains one or more of the constituents in the flow. This use description is applicable also to the other examples described herein, and so will not be described again in detail.

Referring now to FIGS. 3a to 3f, there is illustrated schematically perspective views and a schematic cross section (FIG. 3c) of another example of a part of a device 300 comprising a receptacle section 302 in different configurations. The example receptacle section 302 in FIGS. 3a to 3e can be used, for example as illustrated in the FIGS. 3a to 3e as the mouth-end section of the device 300, or as some other section of the overall device 300, for example, intermediate of the body (not illustrated) of the device 300 and the mouthpiece of the device 300. For brevity, features in FIGS. 3a to 3f and the functioning thereof that are the same or similar to those features already described with reference to FIGS. 2a to 2d are given similar reference numerals to as in FIG. 2 but increased by 100, and will not be described in detail again.

The mouth-end section 302 illustrated in FIGS. 3a to 3f is similar to the mouth-end section 202 illustrated in FIGS. 2a to 2d. As in the mouth-end section 202 illustrated in FIGS. 2a to 2d, the mouth-end section 302 illustrated in FIGS. 3a to 3f comprises a first portion 302a, and a second portion 302b slidably mounted to the first portion 302a thereby to allow sliding movement (arrow Z in FIGS. 3a and 3b) of the second portion 302b relative to the first portion 302a substantially parallel to a longitudinal axis P-P of the mouth-end section 302, between a closed configuration (see FIGS. 3a and 3f) and an open configuration (see FIGS. 3b, 3c, and 3d). The second portion 302b comprises a cylindrical housing 302b into which the first portion 302a is receivable. The first portion 302a extends from a body 306 of the overall device 300. The mouth-end section 302 comprises a biasing means 330, such as a spring 330, to bias the housing 302b away from the body 306 of the overall device, to bias the mouth-end section 302 towards its closed configuration (see FIG. 3a).

In this example, the first portion 302a comprises a plurality of resilient members 338. The resilient members 338 are generally flat and are arranged side by side around the inner wall of the housing 302b when the mouth-end section 302 is in the closed configuration (see FIG. 3a). The resilient members 338 are biased radially outwardly of the longitudinal axis P-P. The resilient members 338 define between them a receiving region 340 for receiving a flavor flavour element 324. The first portion 302a comprises a stem 339 extending from the body 306 of the overall device 300. The resilient members 338 are supported on the stem 339. The resilient members 338 and the stem 339 are receivable in the housing 302b.

Figure 3A:
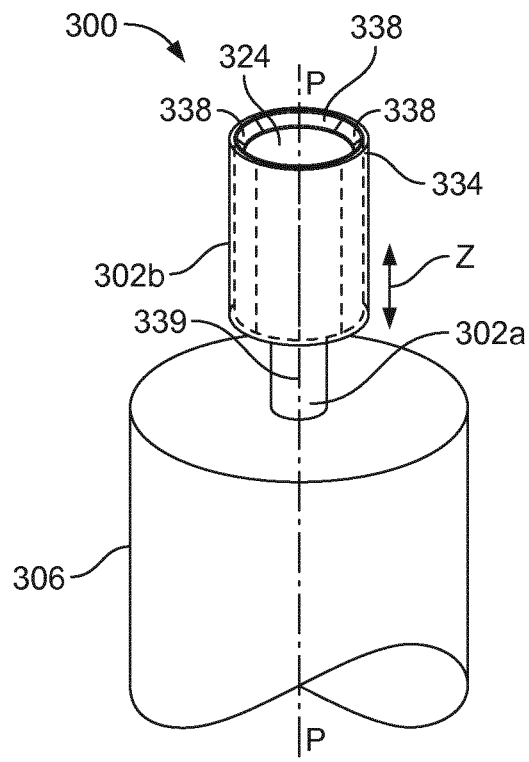
FIGS. 3a to 3f show schematic perspective views, and a schematic cross section of a part of an aerosol provision article comprising a second receptacle section in different configurations according to a second example.
Figure 3B:
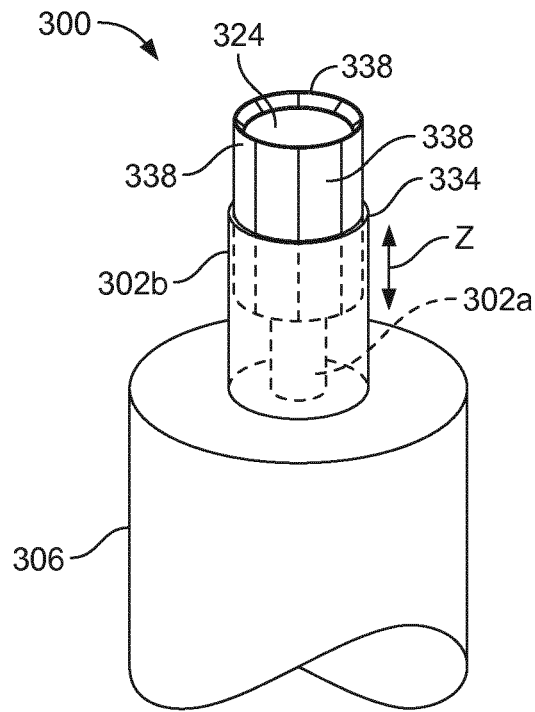
Figure 3C:
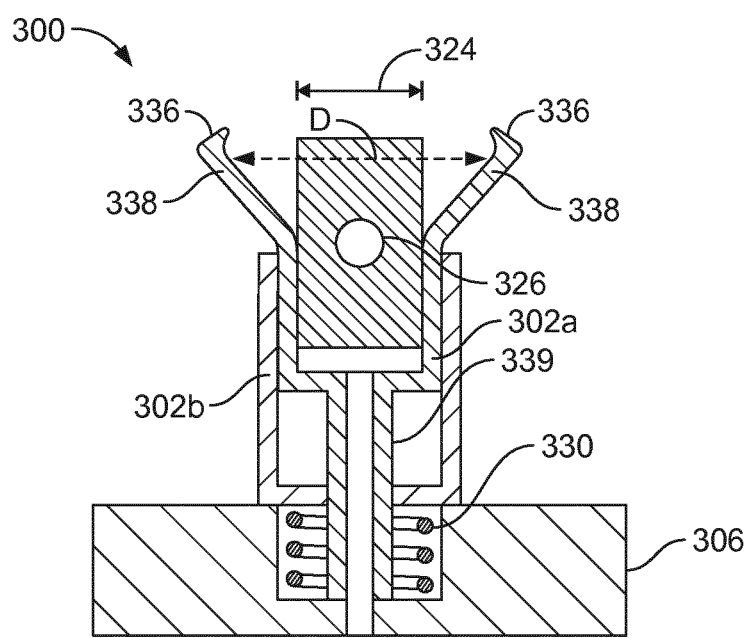
Figure 3D:
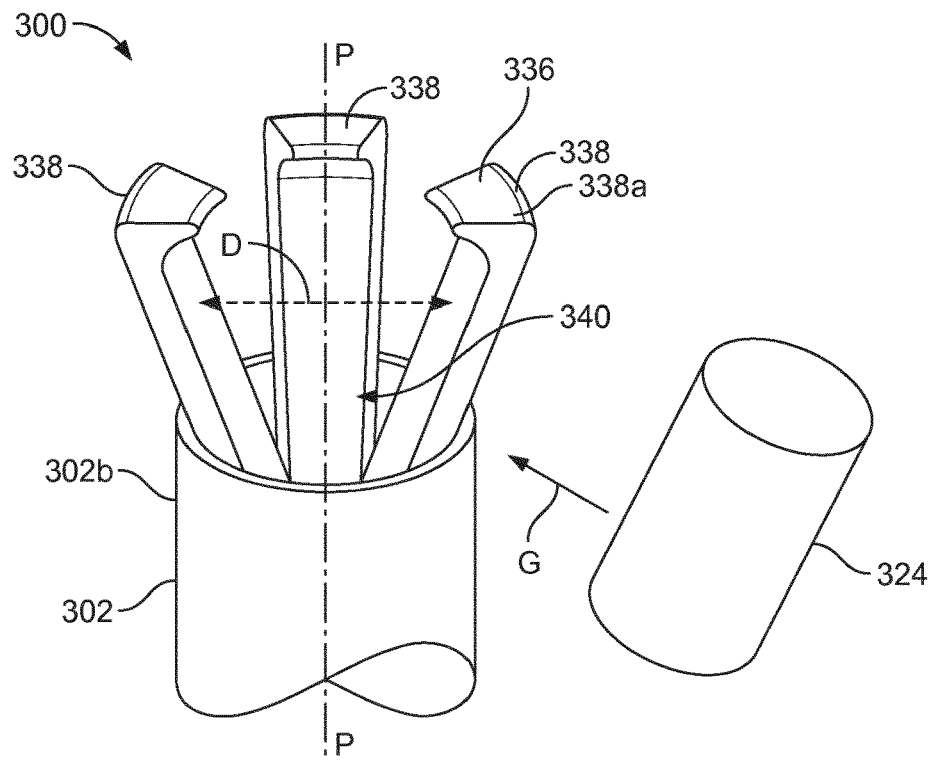
Figure 3E:
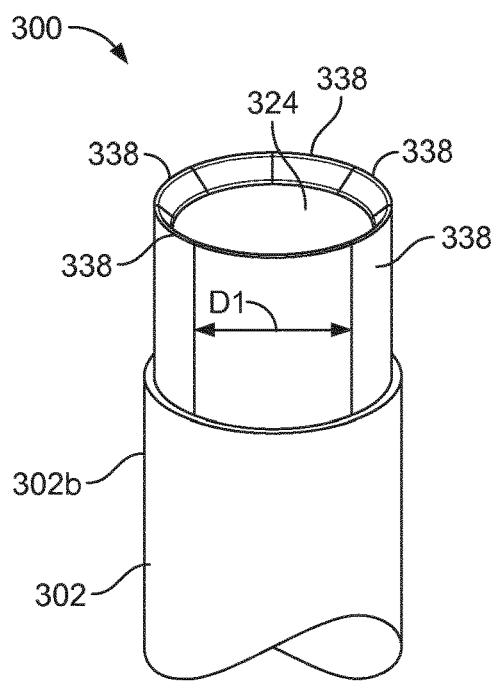
Figure 3F:
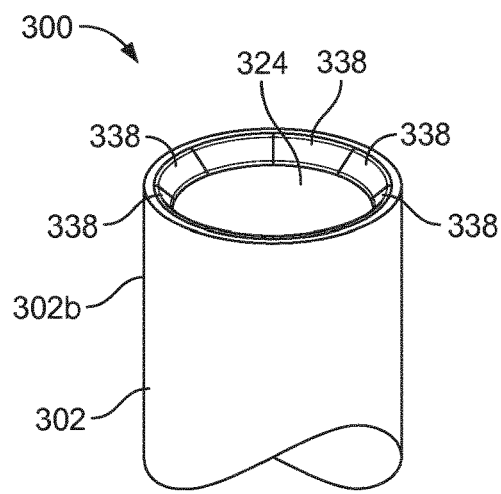

Referring to the sequence illustrated in FIGS. 3a to 3f, the mouth-end section 302 is first in the closed configuration (see FIG. 3a). The housing 302b is located relatively away from the body 306 of the overall device 300, and the resilient members 338 are received in the housing 302b. The resilient members 338 are thereby restricted from moving radially outwardly by the inner wall of the housing 302b. A user may wish to insert, remove, and/or replace a flavor element 324 into and or from the mouth-end section 302. A user may therefore push or otherwise manipulate (see arrow Z in FIG. 3b) the housing 302b to slide substantially parallel to the longitudinal axis P-P of the device 300, relative to the first portion 302a, against the biasing means 330, towards the body 306 of the overall device 300. This causes each of the resilient members 338 to protrude (be exposed) out of an open end 334 of the housing 302b. The mouth-end section 302 is thereby brought into its open configuration (see FIGS. 3b, 3c, and 3d). In this open configuration, the resilient members 338 are not (fully) restricted by the inner wall of the housing 302b, and hence move radially outwardly of each other (see FIGS. 3c and 3d). The resilient members 338 thereby define between them a radial dimension D of the receiving region 340 for allowing the flavor element 324 to be inserted into (and/or removed from) the receiving region 340 (see FIGS. 3c and 3d). A user may insert (see arrow G in FIG. 3d) a flavor element 324 into the receiving region between the resilient members 380. Once the flavor element 324 is inserted into the receiving region 340, a user may cease pushing (or otherwise exerting a force on) the housing 302b towards the body 306 of the device 300, and hence the housing 302b, under the force of the biasing means 330, is forced to slide substantially parallel to the longitudinal axis P-P of the device 300 away from the body 306, back over the resilient members 338 (See FIG. 3e). Alternatively or additionally, the housing 302b may be pulled or otherwise manipulated away from the body 306 and back over the resilient members 338. In either case, the housing 302b thereby slides over the resilient members 338, which causes the resilient members 338 to be forced closer together laterally by the presence of the walls of the housing 302b, thereby to define a smaller radial dimension D1 of the receiving region 324 (the radial dimension D1 in the closed configuration is smaller than the radial dimension D when in the open configuration) (see FIG. 3e). The resilient members 338 thereby grip around the flavor element 324 in the receiving region 324, thereby to retain the flavor element 324 in the mouth-end section 302. The housing 302b is slid over the resilient members 338 until the resilient members 338 are fully received in the housing 302b (see FIG. 3f), and the flavor element 324 is thereby retained therein. The mouth-end section 302 is thereby in the closed configuration (see FIGS. 3e and 3a).

One or more of the resilient members 338 may comprise a lip portion 336, at a distal end 338a of the resilient member 338, that extends radially inwardly of the resilient member 338 thereby to help retain the flavor element 324 in the receiving region 340.

The mouth-end section 302 may comprise a retaining element (not shown) to retain the mouth-end section 302 in the closed configuration. The retaining element (not shown) is operable by a user so that, when operated, the retaining element (not shown) releases the housing 302b so that it may be pushed (or otherwise manipulated) by a user towards the body 306 of the device 300 (i.e. pushed towards the open configuration). A user can conveniently insert, remove, and/or replace a flavor element 324 into the mouth-end section 302.

Referring now to FIGS. 4a to 4d, there is illustrated schematically perspective views of a part of an aerosol provision article 400 with another example receptacle section 402 in different configurations. In this example, the receptacle section 402 is again a mouth-end section 402 of the aerosol provision article 400 although in other examples it may be a receptacle section intermediate of the mouthpiece and the body 406 of the device 400. For brevity, features in FIG. 4 and the functioning thereof that are the same or similar to those features already described with reference to FIGS. 3a to 3e are given similar reference numerals to as in FIGS. 3a to 3e but increased by 100, and will not be described in detail again.

Figure 4A:
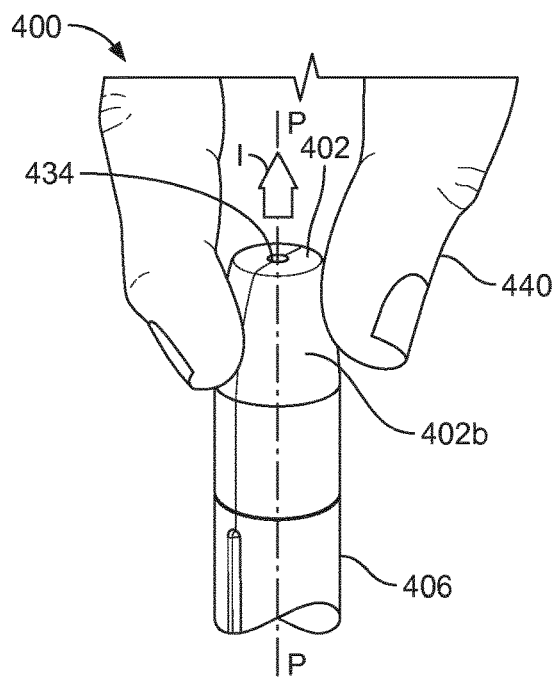
FIGS. 4a to 4d show schematic perspective views of a part of an aerosol provision article comprising a third receptacle section in different configurations according to a third example.
Figure 4B:
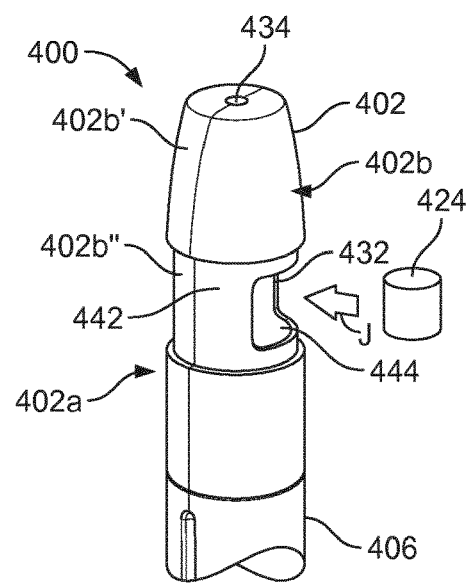
Figure 4C:
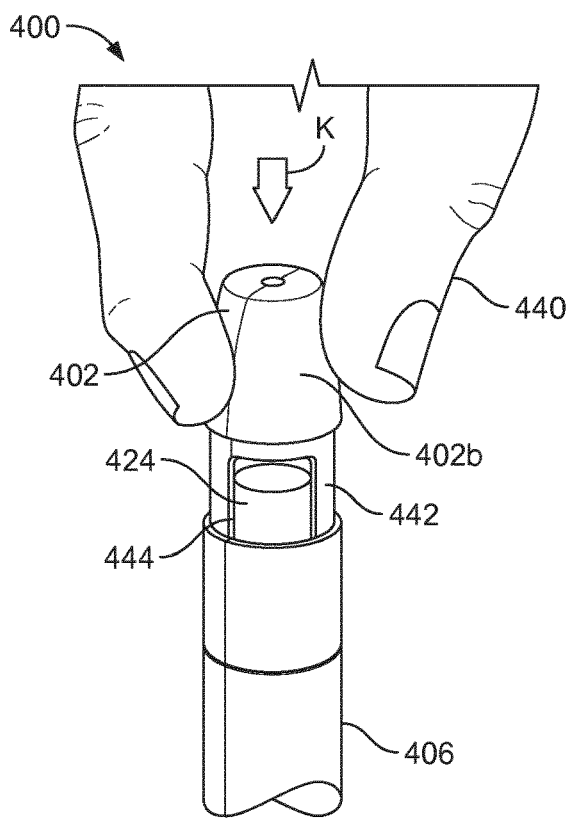
Figure 4D:
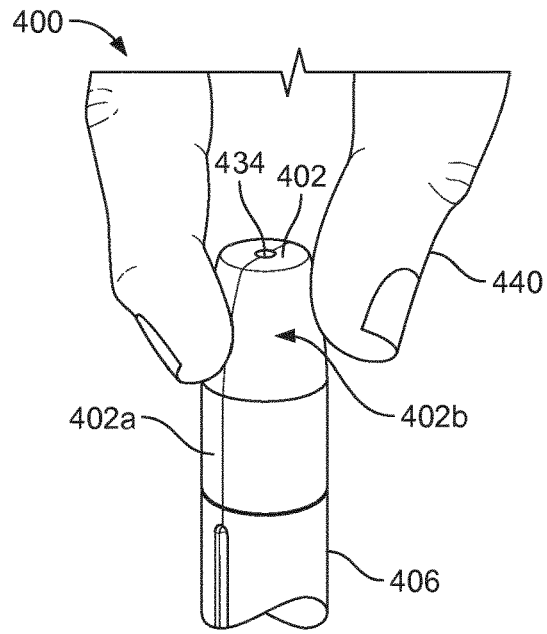

As in the mouth-end section 202 illustrated in FIGS. 2a to 2d, the mouth-end section 402 illustrated in FIGS. 4a to 4d comprises a first portion 402a, and a second portion 402b slidably mounted to the first portion 402a thereby to allow sliding movement of the second portion 402b relative to the first portion 402a substantially parallel to a longitudinal axis P-P of the mouth-end section 402, between a closed configuration (see FIGS. 4a and 4d) and an open configuration (see FIGS. 4b and 4c).

In this example, however, the mouth-end section 402 is arranged to allow insertion and/or removal of a flavor element 424 into and/or from the mouth-end section 402 in a direction substantially perpendicular to the longitudinal axis P-P of the mouth-end section 402.

The first portion 402a and the second portion 402b are generally elongate and are hollow. The first portion 402a extends from the body portion 406 of the device 401 and connects, for example by a screw thread, to the body portion 406. The second portion 402b comprises a first part 402b' and a second part 402b" that extends from the first part 402b' and has a slightly narrower diameter than does the first part 402b' and which is slidably received in the first portion 402a. The mouth-end section 402 defines a flow channel 432 internally thereof. The first part 402b' of the second portion 402b is for receipt into a user's mouth. The first part 402b' of the second portion 402b has an outlet 434 allowing a user to inhale aerosol from the overall device 400 via the channel 432. A side wall 442 of the second part 402b" of the second portion 402b defines an opening 444 for insertion and/or removal of the flavor element 424, through the opening 444, into the channel 432 internal of the second portion 402b.

In the closed configuration (see FIGS. 4a and 4c), the first part 402b' of the second portion 402b abuts against the first portion 402a and the second part 402b" of the second portion 402b is within the first portion 402a such that the opening 444 in the side wall 442 is closed off by the first portion 402a.

In the open configuration (see FIGS. 4b and 4c), the first part 402b' of the second portion 402b is relatively distal from the first portion 402a and the second part 402b" of the second portion 402b is exposed so that the opening 444 is exposed for insertion and/or removal of the flavor element 424 there through.

The mouth-end section 402 allows a user to easily and conveniently insert remove and or replace a flavor element 424 into the mouth-end section 402. The outlet 434 of the first part 402b' of the second portion 402b can be made small enough so as to ensure the flavor element 424 cannot be removed from, or fall out of, the outlet 434, or indeed out of the overall device 400, when the mouth-end section 402 is in the closed configuration. This can improve the safety of using the overall device 400.

Referring to the sequence illustrated in FIGS. 4a to 4d, the mouth-end section 402 of the overall device 400 is initially in a closed configuration (see FIG. 4a). A user 440 may wish to insert, remove, or replace a flavor element 424. The user 440 pulls on or otherwise manipulates (arrow I) the first part 402b' of the second portion 402b away from the first portion 402a by sliding the second part 402b" of the second portion 402b out of the first portion 402a substantially parallel to the longitudinal axis P-P of the mouth-end section 402 so as to be in the open configuration (as in FIG. 4b).

The user may then insert (arrow J) the or another flavor element 424, through the now exposed opening 444 in the side wall 442 into the channel 432 (see FIG. 4b). Once the flavor flavour element 424 is inserted, the user 440 may push or otherwise manipulate (arrow K in FIG. 4c) the first part 402b" of the second portion 402b back towards the first portion 402a, so that the second part 402b" of the second portion 402b slides substantially parallel to axis P-P of the mouth-end section 402 into the first portion 402a so as to be in the closed configuration (as in FIG. 4d).

Referring now to FIGS. 5a to 5d, there is illustrated schematically perspective views of a part of an aerosol provision article 500 with another example receptacle section 502 in different configurations. In this example, the receptacle section is again a mouth-end section 502 although in other examples the receptacle section 502 may be intermediate of the mouthpiece and the body 506 of the device 500. For brevity, features in FIGS. 5a to 5d and the functioning thereof that are the same or similar to those features already described with reference to FIGS. 4a to 4d are given similar reference numerals to as in FIGS. 4a to 4d but increased by 100, and will not be described in detail again.

Figure 5A:
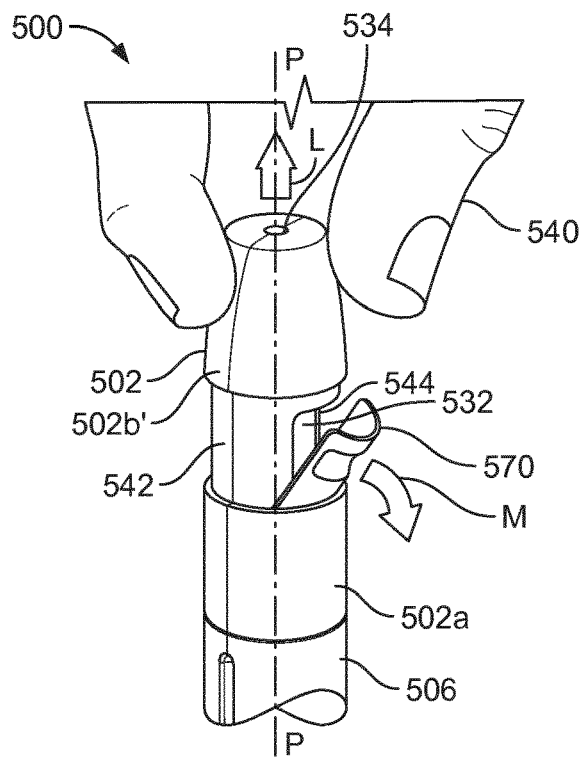
FIGS. 5a to 5d show schematic perspective views of a part of an aerosol provision article comprising a fourth receptacle section in different configurations according to a fourth example.
Figure 5B:
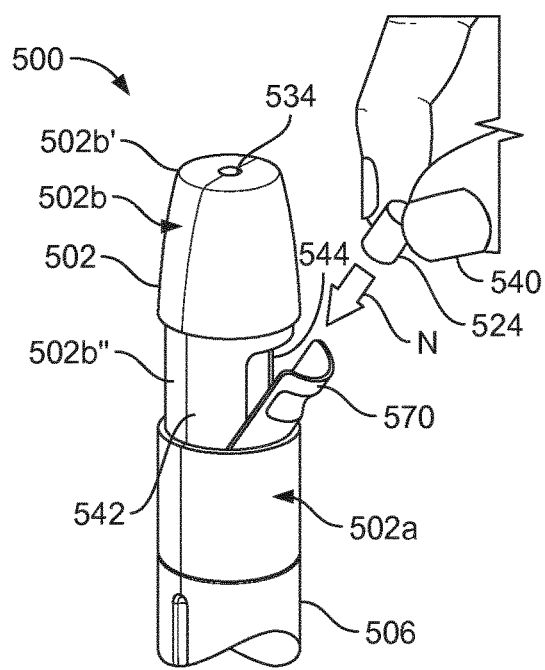
Figure 5C:
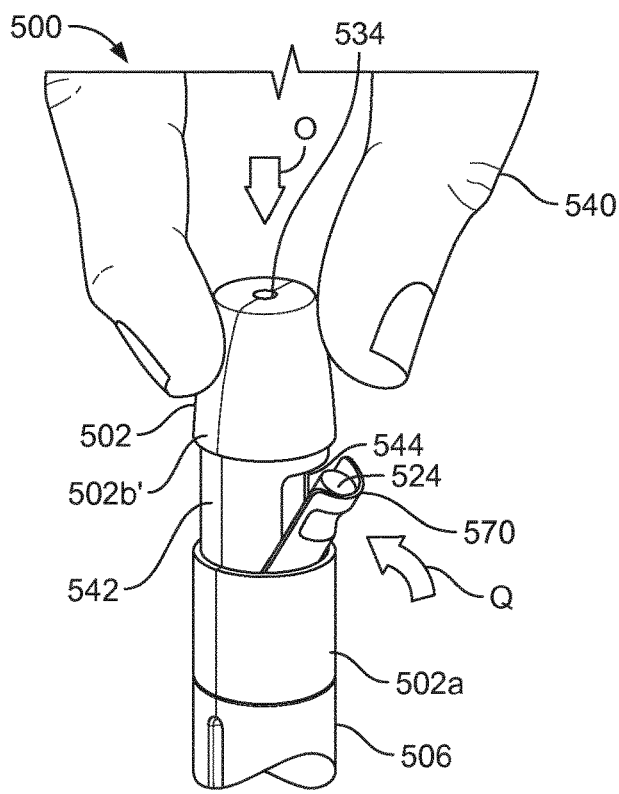

As in the mouth-end section 402 illustrated in FIGS. 4a to 4d, the mouth-end section 502 illustrated in FIGS. 5a to 5d comprises a first portion 502a, and a second portion 502b slidably mounted to the first portion 502a thereby to allow sliding movement of the second portion 502b relative to the first portion 502a substantially parallel to a longitudinal axis P-P of the mouth-end section 502, between a closed configuration (see FIG. 5d) and an open configuration (see FIGS. 5a to 5c). The mouth-end section 502 illustrated in FIGS. 5a to 5d is arranged to allow insertion and/or removal of a flavor element 524 into and/or from the mouth-end section 502 in a direction substantially perpendicular to the longitudinal axis P-P of the mouth-end section 502, through an opening 544 in a side wall 542 of the first portion 502a exposed in the open configuration, into a flow channel. Again, the first portion 502a extends from the body portion 506 of the device 501 and connects, for example by a screw thread, to the body portion 506. The second portion 502b comprises a first part 502b' and a second part 502b" that extends from the first part 502b' and has a slightly narrower diameter than does the first part 502b' and which is slidably received in the first portion 502a. The first part 502b' of the second portion 502b has an outlet 534 for allowing a user to inhale aerosol from the mouth-end section 502.

In this example, however, the mouth-end section 502 further comprises a third portion 570 for closing off the opening 544, the third portion 570 being pivotally mounted to the second part 502b" of the second portion 502b about an axis substantially perpendicular to the longitudinal axis P-P of the mouth-end section 202. The third portion 570 is generally sheet like, but curved to match the curvature of the side wall 542 of the second part 502b" of the second portion 502a. This helps the third portion 570 to effectively close off the opening 544 in the side wall 542 (which is similarly curved).

In the open configuration (see FIGS. 5a to 5c) the third portion 570 is exposed allowing the third portion 570 to pivot relative to the second part 502b" of the second portion 502b, and hence expose the opening 544 in the side wall 542 of second part 502b" of the second portion 502a for insertion, removal or replacement of a flavor element 542 there through.

In the closed configuration (see FIG. 5d) the third portion 570 covers the opening 544 and the second part 502b" of the second portion 502b is inside of the first portion 502a.

The mouth-end section 502 may comprise a biasing means (not shown) to bias the third portion 507 to pivot out and away from second part 502b" of the first portion 502ba. In this case, when the mouth-end section 502 is in the open configuration, the third portion 570 will automatically pivot so as to expose the opening 544 in the side wall 542 of the second part 502b" of the second portion 502b. This allows convenient insertion, removal, or replacement of a flavor element 524 into the channel 532 of the mouth-end section 502.

Figure 5D:
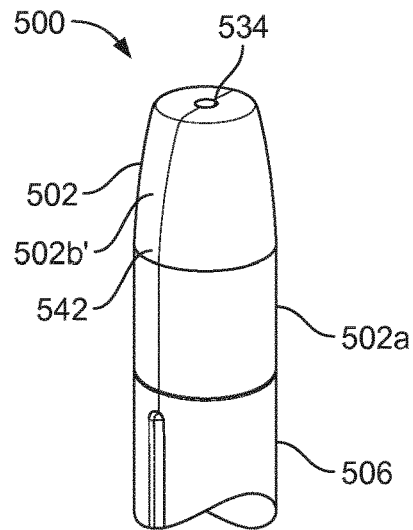

Referring to the sequence illustrated in FIGS. 5a to 5d, from a closed configuration (e.g. that as shown in FIG. 5d) a user 540 may pull or otherwise manipulate (arrow L) the second part 502b" of the second portion 502b away from the first portion 502a, so that the second part 502b" of the second portion 502b slides substantially parallel to the longitudinal axis P-P of the mouth-end section 502 out of the first portion 502a, thereby to expose the second part 502b" of the second portion 502b and the third portion 570 (see FIG. 5a). The third portion 570 may then pivot (arrow M) relative to the second part 502b" of the second portion 502b so as to expose the opening 544 in the side wall 542. The pivoting may occur under gravity, or by manipulation by a user, under the force of a biasing means (not shown) biasing the third portion 507 away from the second part 502b" of the second portion 502b, or by any combination of these. A user 540 may then place (arrow N) (see FIG. 5b) a flavor element 524 onto an inner surface of the third portion 570 and insert the flavor element into the channel 532 by pivoting (arrow C) the third portion 570 into a closed position (see FIG. 5b).

Once the flavor element 524 is inserted, a user 540 may push or otherwise manipulate (arrow O) the first part 502b' of the second portion 502b towards the first portion 502a, thereby causing the second part 502b" of the second portion 502b to slide substantially parallel to the longitudinal axis P-P of the mouth-end section 502 into the closed configuration (FIG. 5d). In so doing, the side wall of the first portion 502a pushes against (urges) the third portion 507 so as to cause the third portion 507 to pivot (arrow Q) so as to become flush with the side wall 542 of the second portion 502b, and thereby to close off the opening 544 (see FIG. 5c). Alternatively a user may manually push the third portion 507 flush with the side wall 542 of the second portion 502b prior to or while pushing the second portion 502b towards the first portion 502a. Once the second portion 502b is pushed so that the side wall 542 and the third portion are fully received in the first portion 502b, the mouthpiece 502 is in the closed configuration, and is ready to use (see FIG. 5d).

The mouth-end section 502 may comprise a retaining element (not shown) that retains the second portion 502b relative to the first portion 502a so that the mouth-end section 502 is retained in the closed configuration unless a significant force (i.e. the force of a user manually pulling on the second portion 502b) is provided.

Figure 6A:
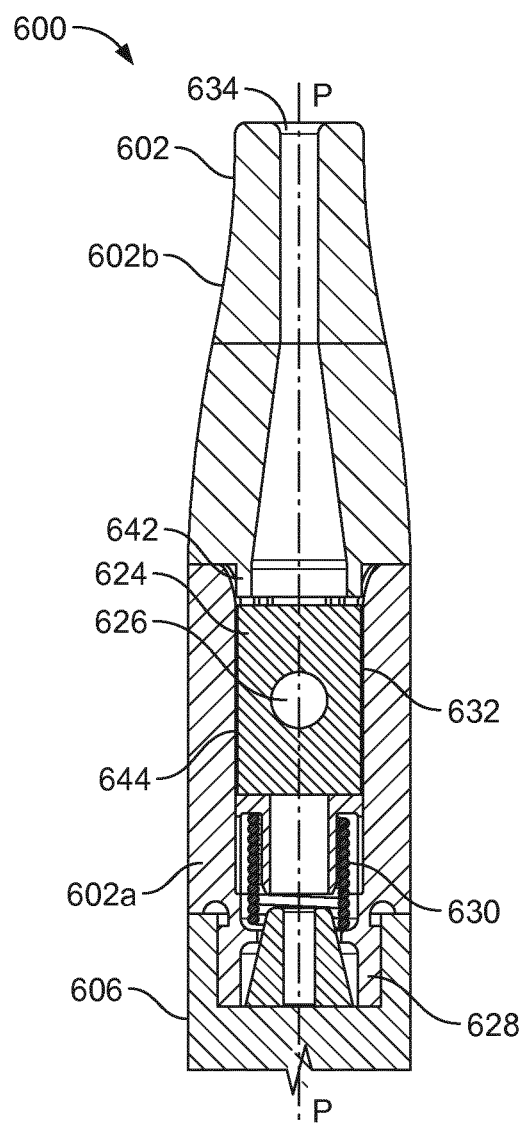
FIGS. 6a and 6b show schematic cross sections of a part of an aerosol provision article comprising a fifth receptacle section in different configurations according to a fifth example.
Figure 6B:
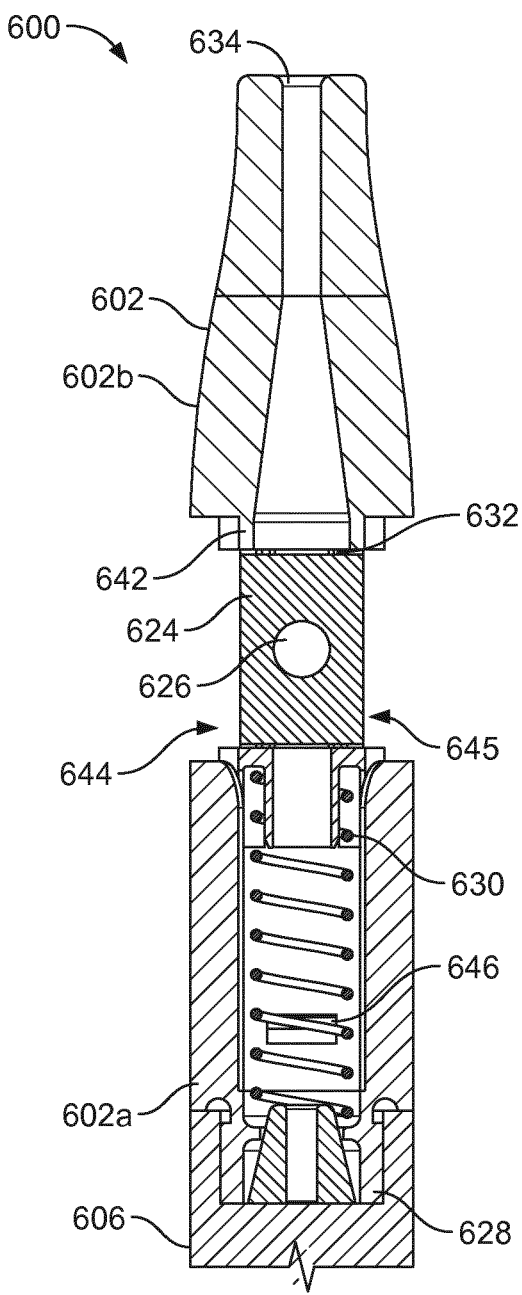

Referring now to FIGS. 6a and 6b, there is illustrated schematically cross sectional views of a part of an aerosol provision article 600 with another example receptacle section 602 in different configurations. In this example, the receptacle section 602 is again a mouth-end section 602. For brevity, features in FIG. 6 and the functioning thereof that are the same or similar to those features already described with reference to FIGS. 5a to 5d are given similar reference numerals to as in FIG. 5 but increased by 100, and will not be described in detail again.

The mouth-end section 602 illustrated in FIGS. 6a and 6b comprises a first portion 602a, and a second portion 602b slidably mounted within the first portion 602a thereby to allow sliding movement of the second portion 602b relative to the first portion 602a substantially parallel to a longitudinal axis P-P of the mouth-end section 602, between a closed configuration (see FIG. 6a) and an open configuration (see FIG. 6b). Similarly to the mouth-end section 402 illustrated in FIGS. 4a to 4d, the mouth-end section 602 illustrated in FIGS. 6a and 6b is arranged to allow insertion and/or removal of a flavor flavour element 624 into and/or from the mouth-end section 602 in a direction substantially perpendicular to the longitudinal axis P-P of the mouth-end section 602, through an opening 644 in a side wall 642 of the second portion 602b exposed in the open configuration, into a channel 632 of the second portion 602b. The second portion 602b has an outlet 634 for allowing a user to inhale aerosol from the mouth-end section 602.

In this example, however, the second portion 602b has a second opening 645 in the side wall 642 of the second portion 602b, the second opening 645 being on an opposite side of the side wall 642 to the opening 644 (now referred to with respect to FIGS. 6a and 6b as the 'first' opening 644). This second opening 645 allows, when the mouth-end section 602 is in the open configuration, for a first flavor element (not shown) to be inserted into the channel 632 of the second portion 602b (e.g. through the first opening 644) whilst simultaneously removing a second flavor 624 installed in the channel 632 element 624 from the channel 632 (e.g. through the second opening 645). This can be achieved, for example, by a user bringing the first flavor element (not shown) up to the first opening 644, and pushing the first flavor element (not shown) laterally against the second flavor element 624, thereby to simultaneously displace the second flavor element 624 from the channel 632 and install the first flavor element (not shown) from the channel 632. The mouth-end section 602 therefore allows rapid and convenient flavor element 624 replacement.

The mouth-end section 602 comprises a connecting means 628 to releasably connect the mouth-end section 602 to a body 606 of the overall device 600. The mouth-end section 602 comprises a biasing means 630, (e.g. a spring 630) mounted within the first portion 602a to bias the second portion 602b away from and out of the first portion 602a towards the open configuration (see FIG. 6b). The first portion 602a comprises a retaining element 646 to releasably retain the second portion 602b in the first portion 602a such that the mouth-end section 602 is in the closed configuration (see FIG. 6a). For example, the retaining element 646 may comprise one or more pins for insertion into corresponding slots (not shown) in the second portion 602b, assembled via a push fit. The retaining element 646 may be operable by a user to manually release the second portion 602b from within the first portion 602a. The second portion 602b, once released, may then automatically slide away from the first portion 602a by action of the biasing means 630 such that the mouth-end section 602 is in the open configuration (see FIG. 6b). This provides for convenient and rapid flavor element exchange. As with all of the examples described herein, the flavor element 624 may comprise a crushable flavor capsule 626.

Figure 7:
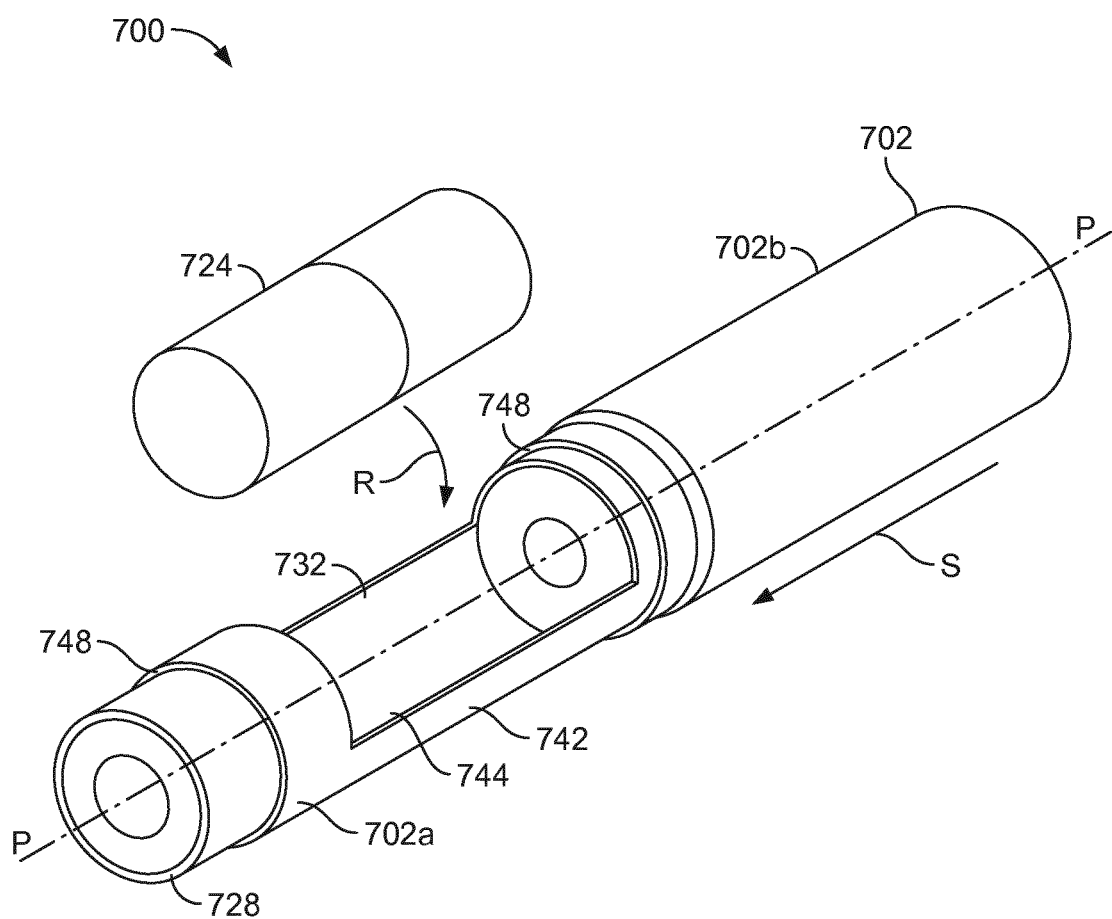
FIG. 7 shows a schematic perspective view of a part of an aerosol provision article comprising a sixth receptacle section according to a sixth example.

Referring now to FIG. 7, there is illustrated schematically a perspective view of a part of an aerosol provision article 700 with another example receptacle section 702 in an open configuration. In this example, the receptacle section 702 is again a mouth-end section 702. For brevity, features in FIG. 7 and the functioning thereof that are the same or similar to those features already described with reference to FIGS. 6a and 6b are given similar reference numerals to as in FIGS. 6a and 6b but increased by 100, and will not be described in detail again.

As in the mouth-end section 402 illustrated in FIGS. 4a to 4b, the mouth-end section 702 illustrated in FIG. 7 comprises a first portion 702a, and a second portion 702b slidably mounted to the first portion 702a thereby to allow sliding movement of the second portion 702b relative to the first portion 702a substantially parallel to a longitudinal axis P-P of the mouth-end section 702, between a closed configuration (not shown) and an open configuration (see FIG. 7). Also, similarly to the mouth-end section 402 illustrated in FIGS. 4a to 4d, the mouth-end section 702 illustrated in FIG. 7 is arranged to allow insertion and/or removal of a flavor element 724 into and/or from the mouth-end section 702 in a direction substantially perpendicular to the longitudinal axis P-P of the mouth-end section 702.

In this example, the first portion 702a is receivable in the second portion 702b. The first portion 702a and the second portion 702b are generally cylindrical in shape. A side wall 742 of the first portion 702a defines an opening 744 through which a flavor element 724 may be inserted into a channel 732 internal of the first portion 702a and extending through the length of the first portion 702a. The first portion 702a is receivable into a channel (not shown) internal of the second portion 702b. The first portion 702a comprises a connecting means 728, such as a screw thread, for connecting to an overall device 700. The second portion 702b is for receipt into a user's mouth, and defines an outlet (not shown) through which a user can inhale aerosol from the mouth-end section 702.

In the open configuration as illustrated in FIG. 7, the second portion 702b is positioned away from the first portion 702a substantially parallel to the longitudinal axis P-P of the mouth-end section 702 so as to expose the opening 744 in the side wall 742 of the first portion 702a for insertion (arrow R), removal, or replacement the flavour element 724 into the channel 732 through the opening 744. Once inserted, a user may slide (arrow S) the second portion 702b back towards the first portion 702b such that the second portion 702b closes off (not shown) the opening 744 of the first portion 702a. The mouth-end section 702 is thereby in the closed configuration (not shown).

The first portion 702a comprises one or more seals 748 on an outer surface of the side wall 742 of the first portion 702a, the seals 748 extending around the circumference of the side wall 742 of the first portion 702a, above and below the opening 748. The seals 738 may be made of a suitable flexible material such as rubber or silicone, for example. The seals 738 are receivable, along with the first portion 702a, in the channel (not shown) of the second portion 702b. The seals 738 act to form a seal, such as an air tight seal, between the first portion 702a and the second portion 702b, when the mouth-end section 702 is in the closed configuration (not shown). This prevents unwanted inlet of air into the channel 732 of the first portion 702a through the opening 744 of the first portion 702a when the mouth-end section 702 is in the closed configuration (not shown).

Figure 8A:
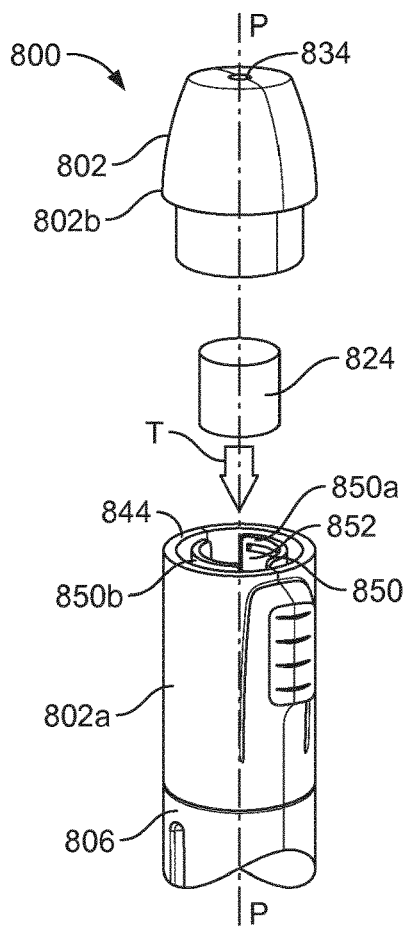
FIGS. 8a to 8c show schematic perspective views of a part of an aerosol provision article comprising a seventh receptacle section in different configurations according to a seventh example.
Figure 8B:
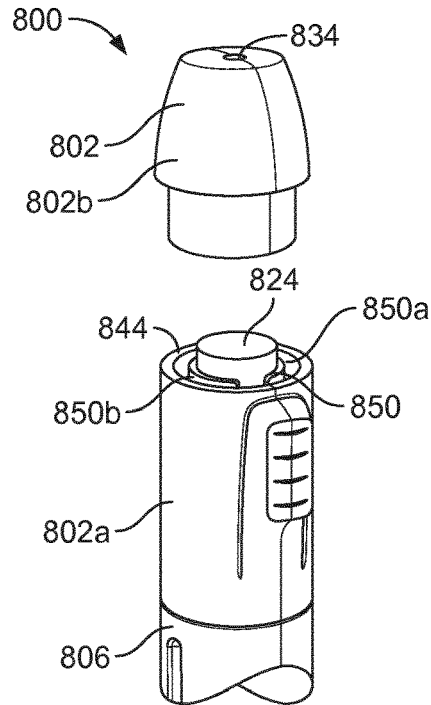
Figure 8C:
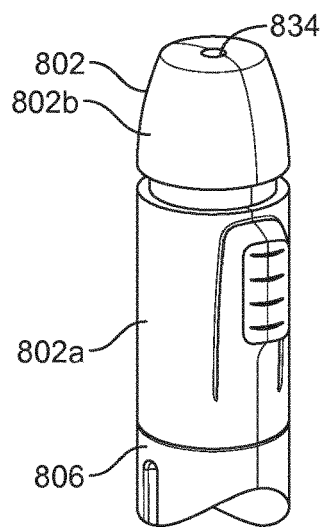

Referring now to FIG. 8, there is illustrated schematically perspective views of a part of an aerosol provision article 800 with another example receptacle section 802 in an open configuration (FIGS. 8a and 8b) and in a closed configuration (FIG. 8c). In this example, the receptacle section 802 is again a mouth-end section 802. For brevity, features in FIG. 8 and the functioning thereof that are the same or similar to those features already described with reference to FIG. 7 are given similar reference numerals to as in FIG. 7 but increased by 100, and will not be described in detail again.

As in the mouthpiece 402 illustrated in FIGS. 4a to 4b, the mouth-end section 802 illustrated in FIGS. 8a to 8c comprises a first portion 802a and a second portion 802b that are generally cylindrical in shape, and the second portion 802b is receivable in the first portion 802a thereby to allow movement of the second portion 802b relative to the first portion 802a substantially parallel to a longitudinal axis P-P of the mouth-end section 802, between a closed configuration (see FIG. 8c) and an open configuration (see FIGS. 8a and 8b).

In this example, however, the second portion 802b is entirely removable from the first portion 802a, the mouth-end section 802 being in the open configuration when the second portion 802b is removed from the first portion 802a, and the mouth-end section 802 being in the closed configuration when the second portion 802b is not removed from the first portion 802a (i.e. is received in the first portion 802a). The second portion 802b is for receipt in a user's mouth and defines an outlet 834 for a user to inhale aerosol from the mouth-end section 802. The first portion 802a has an open end 844 into which the second portion 802b may be removably received.

The first portion 802a comprises a receiving portion 850 housed in the first portion 802 at the open end 844. The receiving portion 850 allows, when the second portion 802b is removed, insertion, removal or replacement of a flavor element 824 into and/or from the receiving portion 850 in a direction substantially parallel to the longitudinal axis P-P of the mouth-end section 802. The receiving portion 850 comprises a plurality of (in this example two) resilient members 850a, 850b extending in a direction substantially parallel to the longitudinal axis P-P of the mouth-end section 802. The resilient members 850a, 850b define between them a receiving region 852 for receiving the flavor element 824 axially therein. The receiving portion 850 is arranged such that when a flavor element 824 is received in the receiving portion 850, at least a portion of the flavor element 824 protrudes out of the receiving portion 824 in a direction substantially parallel to the longitudinal axis P-P of the mouth-end section 802. This ensures that, when the second portion 802b is removed from the first portion 802a, and hence the mouth-end section 802 is in the open configuration, a user can easily manually remove and e.g. replace the flavor element 824 received in the receiving portion 850.

Referring to the sequence of FIGS. 8a to 8c, the second portion 802b is removed from the first portion 802a e.g. by a user (not shown) pulling on or otherwise manipulating the second portion 802b away from the first portion 802a. The mouth-end section 802 is therefore in the open configuration (see FIG. 8a). A user (not shown) may then insert or push (arrow T) a flavor element 824 axially into the receiving region 852 of the receiving portion 850 of the first portion 802a. The flavor element 824 is thereby received in the first portion 802a, but protrudes out beyond the first portion 802a (see FIG. 8b). The user (not shown) may then push (or otherwise manipulate) the second portion 802b into the first portion 802a, thereby to close the open end 844 of the first portion. The mouth-end section 802 is thereby in the closed configuration (see FIG. 8c).

Figure 9:
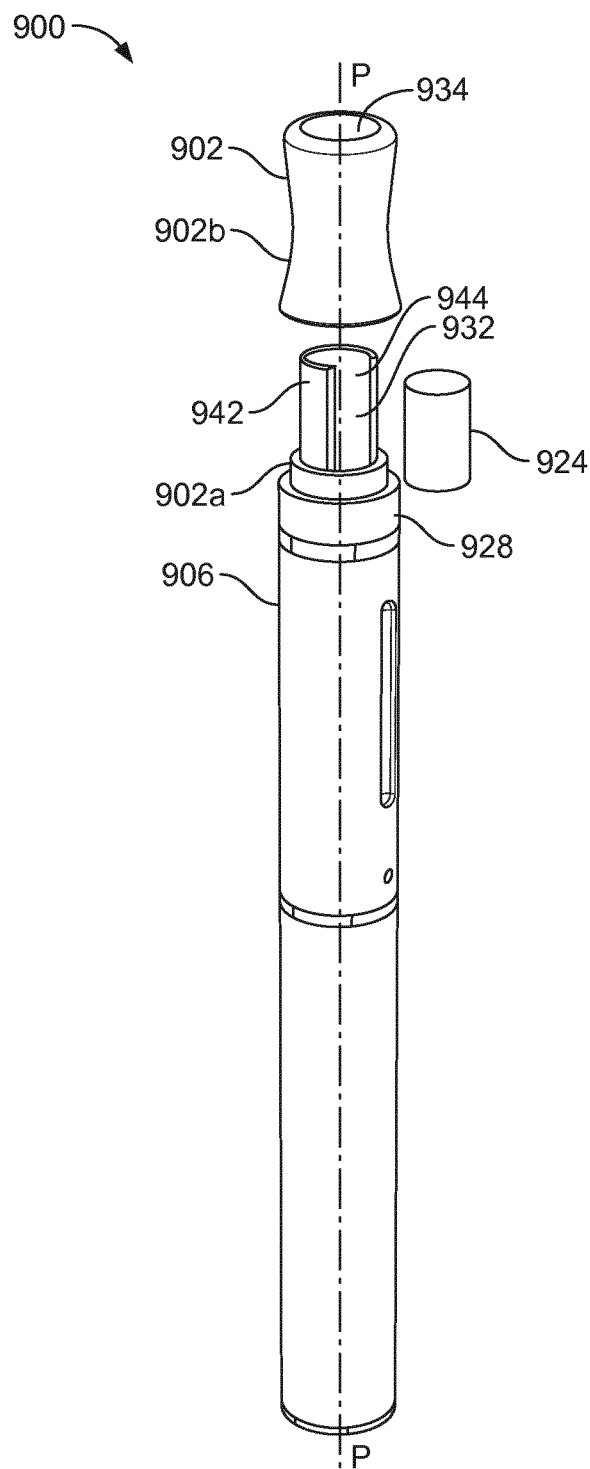
FIG. 9 shows a schematic perspective view of a part of an aerosol provision article comprising an eighth receptacle section according to an eighth example.

Referring now to FIG. 9, there is illustrated schematically a perspective view of an aerosol provision article 900 with another example receptacle section 902 in an open configuration. In this example, the receptacle section 902 is again a mouth-end section 902. For brevity, features in FIG. 9 and the functioning thereof that are the same or similar to those features already described with reference to FIG. 8 are given similar reference numerals to as in FIG. 8 but increased by 100, and will not be described in detail again.

As in the mouth-end section 802 illustrated in FIGS. 8a to 8c, the mouth-end section 902 illustrated in FIG. 9 comprises a first portion 902a and a second portion 902b removable from the first portion 902a, which are arranged to allow movement of the second portion 902b relative to the first portion 902a substantially parallel to a longitudinal axis P-P of the mouth-end section 902. The first portion 902a and the second portion 902b are both generally cylindrical in shape. The mouth-end section 902 is in the open configuration when the second portion 902b is removed from the first portion 902a (see FIG. 9), and is in the closed configuration when the second portion 902b is not removed from the first portion 902a (not shown). The first portion 902a comprises a connecting element 928 for releasably connecting the mouth-end section 902 to a body 906 of the overall device 900. The second portion 902b is for receipt in a user's mouth and defines an outlet 934 for a user to inhale aerosol from the mouth-end section 902.

In this example, however, the first portion 902a is receivable in the second portion 902b, and the mouth-end section 902 is arranged to allow insertion and/or removal of a flavor element 924 into and/or from the mouth-end section 902 in a direction substantially perpendicular to the longitudinal axis P-P of the mouth-end section 402. Specifically, a side wall 942 of the first portion 902a defines an opening 944 through which a flavor element 924 can be inserted into a channel 932 of the first portion 902a. The opening 944 extends the length of the first portion 902a such that the first portion 902a is open sided.

A user (not shown) may remove the second portion 902b from the first portion 902a e.g. by a user (not shown) pulling on or otherwise manipulating the second portion 902b away from the first portion 902a. The mouth-end section 902 is therefore in the open configuration (see FIG. 9). A user (not shown) may then insert or push a flavor flavour element 924 in an axial or radial direction through the opening 944 and into the channel 932 of the first portion 902a. The user (not shown) may then push (or otherwise manipulate) the second portion 902b onto the first portion 902a, thereby to return the mouth-end section 902 to the closed configuration.

Figure 10A:
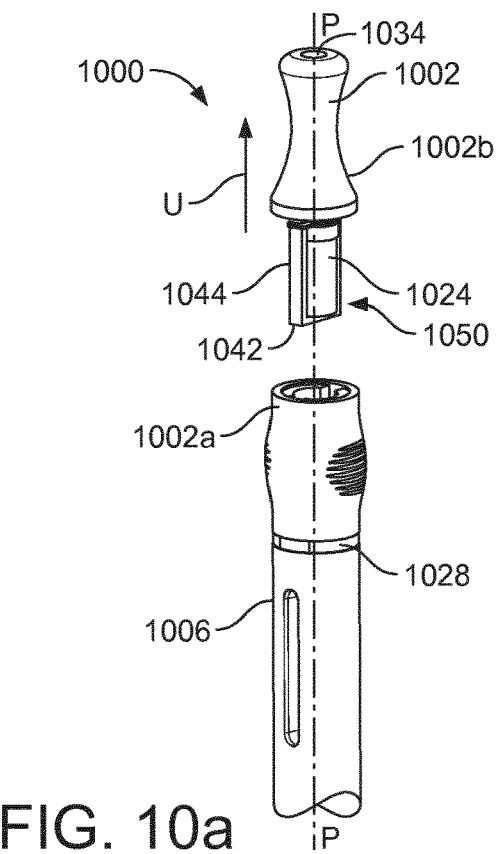
FIGS. 10a to 10d show schematic perspective views of a part of an aerosol provision article comprising a ninth receptacle section in different configurations according to a ninth example.
Figure 10B:
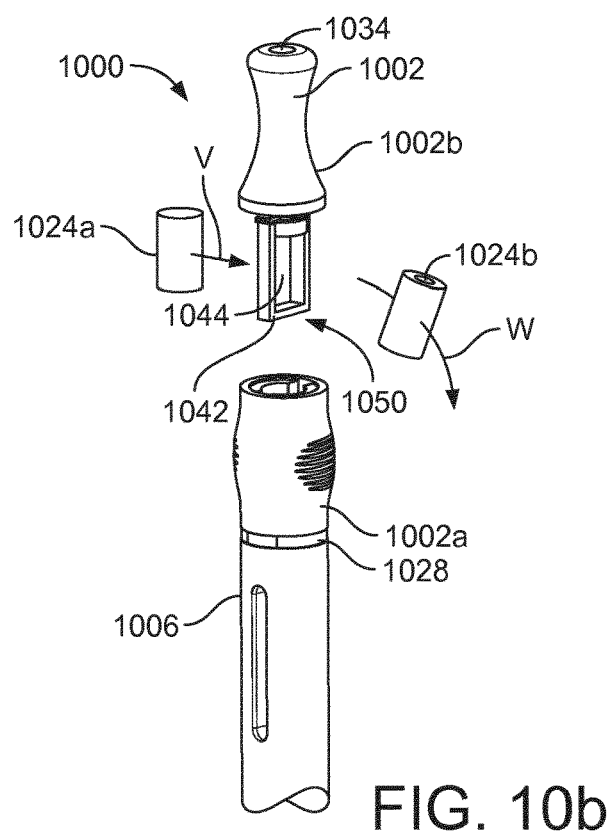
Figure 10C:
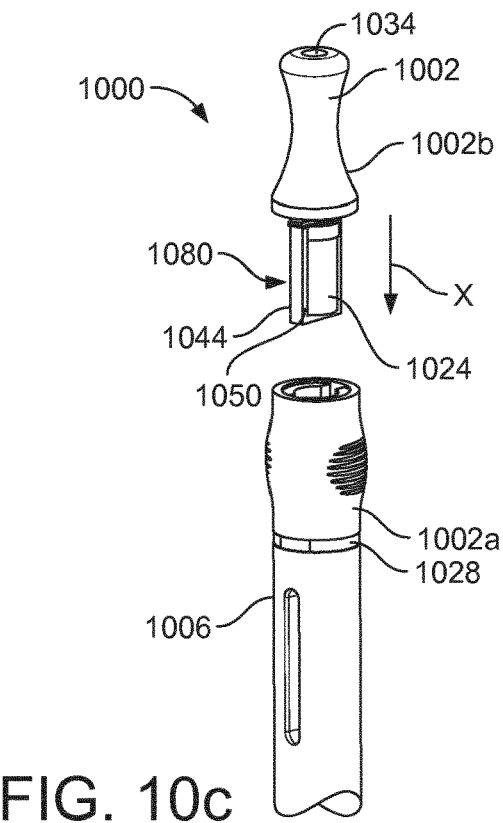
Figure 10D:
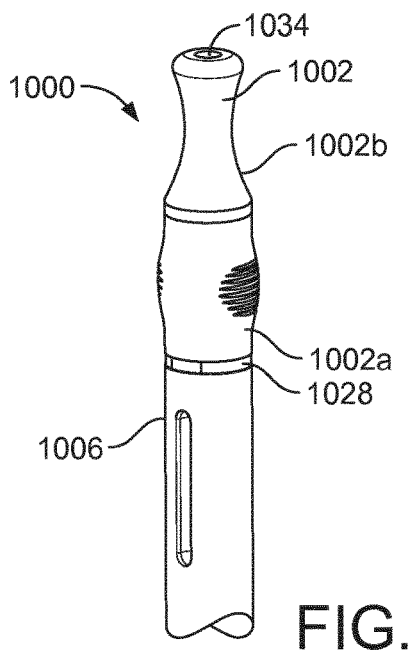

Referring now to FIGS. 10a to 10d, there is illustrated schematically perspective views of a part of an aerosol provision article 1000 with another example receptacle section 1002 in an open configuration (FIGS. 10a to 10c) and a closed configuration (FIG. 10d). In this example, the receptacle section 1002 is again a mouth-end section 1002. For brevity, features in FIG. 10 and the functioning thereof that are the same or similar to those features already described with reference to FIG. 9 are given similar reference numerals to as in FIG. 9 but increased by 100, and will not be described in detail again.

As in the mouth-end section 902 illustrated in FIG. 9, the mouth-end section 1002 illustrated in FIG. 10 comprises a first portion 1002a and a second portion 1002b removable from the first portion 1002a and arranged to allow movement of the second portion 1002b relative to the first portion 1002a substantially parallel to a longitudinal axis P-P of the mouth-end section 1002. The mouth-end section 1002 is arranged to allow, when in the open configuration, insertion and/or removal of a flavor element 1024 into and/or from the mouth-end section 1002 in a direction substantially perpendicular to the longitudinal axis P-P of the mouth-end section 1002. The mouth-end section 1002 is in the open configuration when the second portion 1002b is removed from the first portion 1002a (see FIGS. 10a to 10c), and is in the closed configuration when the second portion 1002b is not removed from the first portion 1002a i.e. received into the first portion 1002a (see FIG. 10d). The first portion 1002a comprises a connecting element 1028 for releasably connecting the mouth-end section 1002 to a body 1006 of the overall device 1000. The second portion 1002b is for receipt in a user's mouth and defines an outlet 1034 for a user to inhale aerosol from the mouth-end section 1002.

In this example, however, the second portion 1002b comprises a receiving portion 1050 that is receivable in the first portion 1002a, for allowing, when the second portion 1002b is removed, insertion and/or removal of the flavor element 1024 into and/or from the receiving portion 1050 in a direction substantially perpendicular to the longitudinal axis P-P of the mouth-end section 1002. Specifically, the receiving portion 1050 of the second portion 1002b defines an aperture 1044 into which the flavor element 1024 can be inserted to be supported by the receiving portion 1050.

Similarly to as the mouth-end section 602 as illustrated in FIGS. 6a and 6b, the mouth-end section 1002 illustrated in FIGS. 10a to 10d allows, when the mouth-end section 1002 is in the open configuration, for a first flavor element 1024a to be inserted into the second portion 1002b (e.g. through a first side of the aperture 1044) whilst simultaneously removing a second flavor 1024b installed in the second portion 1002b through a second side of the aperture 1044.

Referring to the sequence shown in FIGS. 10a to 10d, a user (not shown) may remove the second portion 1002b from the first portion 10002a by pulling or otherwise manipulating (arrow U) the second portion 1002b away from the first portion 1002a substantially parallel to the longitudinal axis P-P of the mouth-end section 1002 (FIG. 10a). The receiving portion 1050 is thereby exposed, and the mouth-end section 1002 is in the open configuration (FIG. 10a). A user (not shown) may then bring the first flavor element 1024a up to the aperture 1044, and push (arrow V) the first flavor element 1024a laterally against the second flavor element 1024b received in the receiving portion 1050, thereby to displace (arrow W) the second flavor element 1024 from receiving portion 1050 out of the aperture 1044 (FIG. 10b). The first flavor element 1024a is thereby installed in the receiving portion 1050 (FIG. 10c). A user may then push or otherwise manipulate (arrow X) the second portion 1002a so as to be received into the first portion 1002a (FIG. 10c). The mouth-end section 1002 is thereby in the closed configuration (FIG. 10d). The mouth-end section 1002 therefore allows rapid and convenient flavor element 1024 replacement.

Figure 11A:
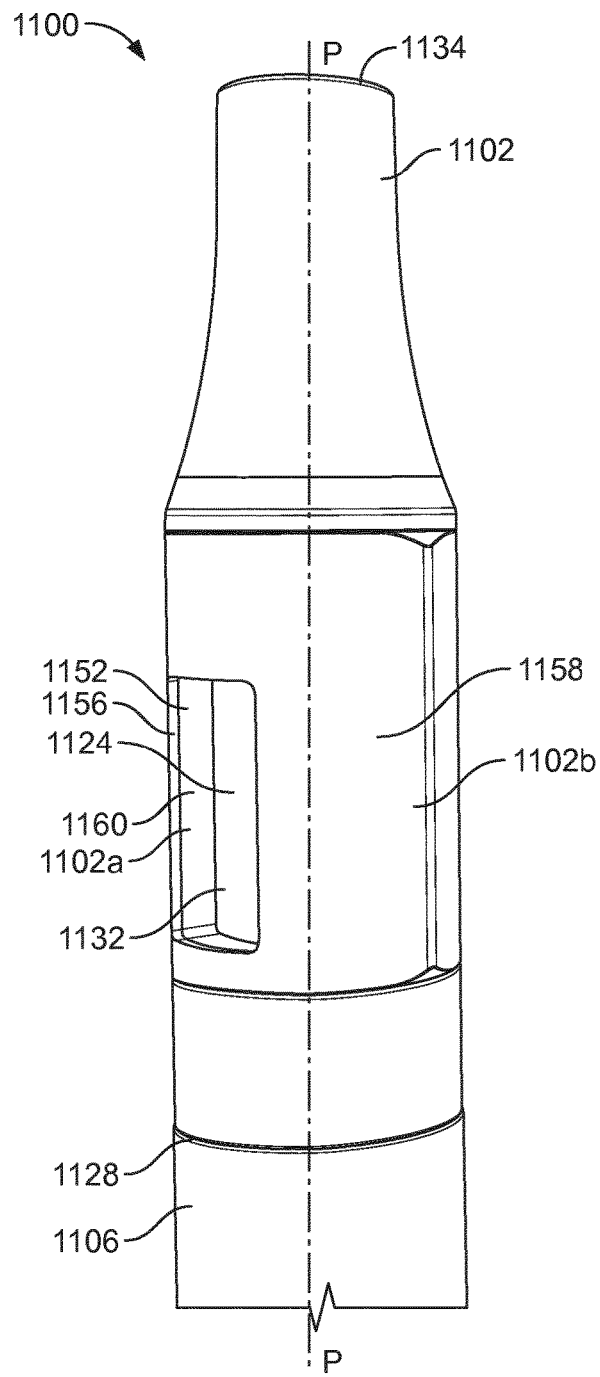
FIGS. 11a and 11b show schematic perspective views of a part of an aerosol provision article comprising a tenth receptacle section in different configurations according to a tenth example.
Figure 11B:
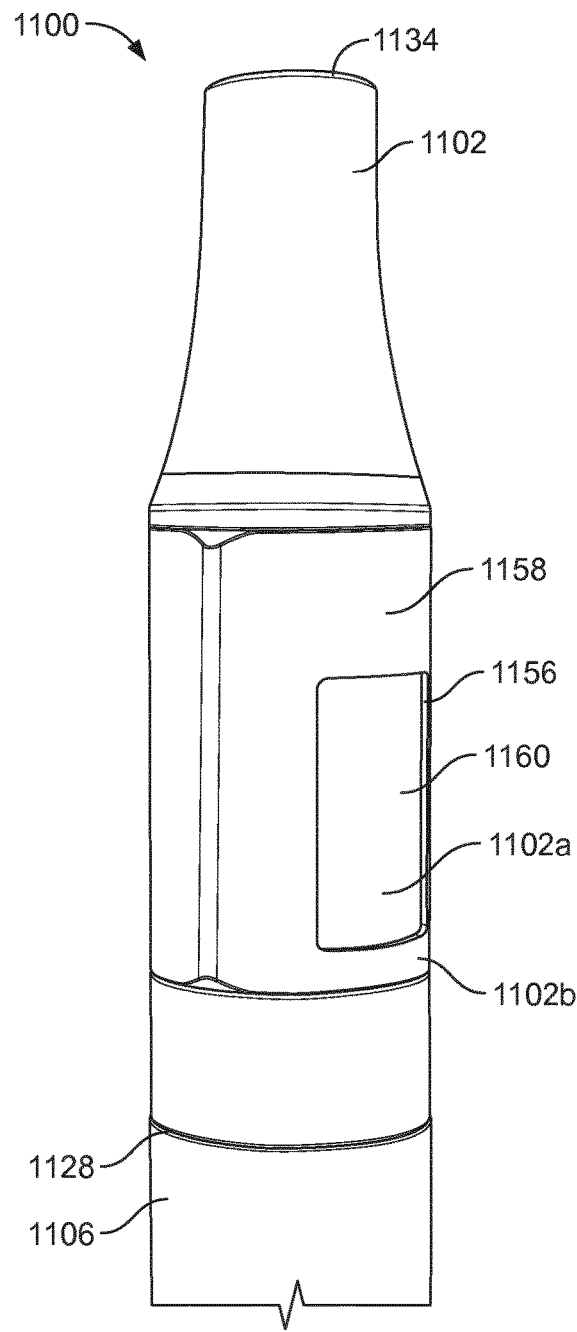

Referring now to FIGS. 11a and 11b, there is illustrated schematically perspective views of a part of an aerosol provision article 1100 with another example receptacle section 1102 in an open configuration (FIG. 11a) and a closed configuration (FIG. 11b). In this example, the receptacle section 1102 is again a mouth-end section 1102. For brevity, features in FIG. 11 and the functioning thereof that are the same or similar to those features already described with reference to FIG. 10 are given similar reference numerals to as in FIG. 10 but increased by 100, and will not be described in detail again.

As in the mouth-end section 1002 illustrated in FIGS. 10a to 10d, the mouth-end section 1102 illustrated in FIGS. 11a and 11*b* comprises a first portion 1102*a* and a second portion 1102*b* received in the first portion 1102*a*. The second portion 1102*b* is moveable relative to the first portion 1102*a* between the open configuration (FIG. 11*a*) and the closed configuration (FIG. 11*b*). The mouth-end section 1102 is arranged to allow, when in the open configuration, insertion and/or removal of a flavor element 1124 into and/or from the mouth-end section 1102 in a direction substantially perpendicular to the longitudinal axis P-P of the mouth-end section 1102. The first portion 1102*a* comprises a connecting element 1128 for releasably connecting the mouth-end section 1102 to a body 1106 of the overall device 1100. The second portion 1102*b* is for receipt in a user's mouth and defines an outlet 1134 for a user to inhale aerosol from the mouth-end section 1102.

In this example, however, the movement of the second portion 1102*b* relative to the first portion 1102*a* comprises rotation about the longitudinal axis P-P of the mouth-end section 1102. Specifically, the second portion 1102*b* is received in, and rotationally mounted with respect to, the first portion 1102*a*, thereby to allow the second portion 1102*b* to rotate about the first portion 1102*a*, between the open configuration (FIG. 11*a*) and the closed configuration (FIG. 11*b*).

A side wall 1160 of the first portion 1102*a* defines an opening 1152. A side wall 1158 of the second portion 1102*b* defines an opening 1156. When the mouth-end section 1102 is in the open configuration (FIG. 11*a*), the opening 1152 of the first portion 1102*a* and the opening 1156 of the second portion 1102*b* are aligned with respect to one another. This allows insertion and/or removal of the flavor element 1124 into and/or from a channel 1132 internal of the first portion 1102*a*, through the opening 1152 of the first portion 1102*a* and the opening 1156 of the second portion 1102*b*. A user (not shown) may then rotate the second portion 1102*b* about the first portion 1102*a* about the longitudinal axis P-P of the mouth-end section (e.g. in a counter-clockwise direction as viewed from the end of the mouth-end section 1102 defining the outlet 1134) thereby to misalign the opening 1152 of the first portion 1102*a* and the opening 1156 of the second portion 1102*b* with respect to one another such that the side wall 1158 of the second portion 1102*b* closes off the opening 1152 of the first portion 1102*a*. The mouth-end section 1102 is thereby in the closed configuration (FIG. 11*b*).

To return the mouth-end section 1102 to the open configuration, a user may rotate the second portion 1102*b* about the first portion 1102*a* about the longitudinal axis P-P of the mouth-end section (e.g. in a clockwise direction as viewed from the end of the mouth-end section 1102 defining the outlet 1134) thereby to align the opening 1152 of the first portion 1102*a* and the opening 1156 of the second portion 1102*b* with respect to one another (FIG. 11*a*). A user may then insert, remove, and/or replace a flavor element 1124 as desired.

In both the open and closed configurations, the second portion 1102*b* is entirely received in the first portion 1102*a*, and hence the mouth-end section 1102 provides a space efficient way to allow convenient manual insertion, removal and/or replacement of a flavor element 1124.

Referring now to FIGS. 12*a* and 12*b*, there is illustrated schematically cross sections of a part of an aerosol provision article 1200 with another example receptacle section 1202 in an open configuration (FIG. 12*a*) and a closed configuration (FIG. 12*b*). In this example, the receptacle section 1202 is again a mouth-end section 1202. For brevity, features in FIG. 12 and the functioning thereof that are the same or similar to those features already described with reference to FIG. 11 are given similar reference numerals to as in FIG. 11 but increased by 100, and will not be described in detail again.

As in the mouth-end section 1102 illustrated in FIGS. 11*a* and 11*b*, the mouth-end section 1202 illustrated in FIGS. 12*a* and 12*b* comprises a first portion 1202*a* and a second portion 1202*b*. The second portion 1202*b* is moveable relative to the first portion 1202*a* between the open configuration (FIG. 12*a*) and the closed configuration (FIG. 12*b*). The mouth-end section 1202 is arranged to allow insertion and/or removal of a flavor element 1224 into and/or from the mouth-end section 1202 in a direction substantially perpendicular to the longitudinal axis P-P of the mouth-end section 1202. The first portion 1202*a* comprises a connecting element 1228 for releasably connecting the mouth-end section 1202 to a body 1206 of the overall device 1200.

In this example, however, the movement of the second portion 1202*b* relative to the first portion 1202*a* comprises rotation about an axis 1268 substantially perpendicular to the longitudinal axis P-P of the mouth-end section 1202. Specifically, the second portion 1202*b* is pivotally mounted 1268 to the first portion 1202*a*, thereby to allow pivoting of the second portion 1202*a* relative to the first portion 1202*a*, about an axis 1268 substantially perpendicular to the longitudinal axis P-P of the mouth-end section, between the open configuration (FIG. 12*a*) and the closed configuration (FIG. 12*b*). A portion 1202*c* is for receipt in a user's mouth and defines an outlet 1234 for a user to inhale aerosol from the mouth-end section 1202. As illustrated in the figures, the third portion 1202*c* may be connected to the first portion 1202*a*, for example snap-fitted, or the third portion 1202*c* and the first portion 1202*a* may be a single integral part.

A side wall 1242 of the first portion 1202*a* defines an opening 1244 allowing insertion and/or removal of the flavor element 1224 into and/or from a channel 1232 internal of the first portion 1202*a* through the opening 1244. The first portion 1202*a* is generally cylindrical, and the second portion 1202*b* is generally curved to match the curvature of the side wall 1242 of the first portion 1202*a* at the opening 1244. When the mouth-end section 1202 is in the open configuration (FIG. 12*a*) the second portion 1202*b* is pivoted out and away from the first portion 1202*a*, thereby exposing the opening 1244 of the first portion 1202*a*. The pivoting of the second portion 1202*b* out and away from the first portion 1202*a* may be restricted to within a range of angles. For example, the pivoting may be restricted (for example by a stop (not shown)) such that the angle that a plane of the second portion 1202*b* makes with respect the longitudinal axis P-P of the apparatus is restricted to between 0° and 90°, for example between 0° and 45°. When the mouth-end section 1202 is in the closed configuration (FIG. 12*b*), the second portion 1202*b* is pivoted towards the first portion so as to close off the opening 1224. In the closed configuration (FIG. 12*b*), an outer surface of the second portion 1202*b* is flush with an outer surface of the side wall 1242 of the first portion 1202*a*. The second portion 1202*b* being generally curved to match the curvature of the side wall 1242 of the first portion 1202*a* at the opening 1244 helps the second portion 1202*b* to effectively close off the opening 1244.

The second portion 1202*b* comprises a protrusion or shelf 1290 that extends out at or near a right angle to the plane of the second portion 1202*b*. The shelf 1290 is for supporting a flavor element 1224 in the second portion 1202*b*. This can be useful, for example, to support the flavor element 1224 in the second portion 1202*b* when the mouth-end section 1202 is in the open configuration (FIG. 12*a*), thereby allowing for convenient manual insertion, removal and/or replacement of the flavor element 1224 into and/or from the mouth-end section 1202.

The first portion 1202a comprises a retaining element 1264 to releasably retain the second portion 1202b in the closed configuration. Specifically, the retaining element 1264 comprises a protrusion or latch 1264a. The latch 1264a is releasably receivable in a recess or notch 1291 in the shelf 1290 of the second portion 1202b. When the mouth-end section 1202 is in the closed configuration, the latch 1264a is received in the notch 1291 thereby to retain or latch the second portion in the closed configuration. The mouth-end section 1202 comprises a biasing means, such as a spring 1266, to bias the retaining element 1264 for receipt of the latch 1264a in the notch 1291. The latch 1264 is operable by a user (not shown), against the spring 1266, to release the latch 1264 from the notch 1291, thereby to release the second portion 1202b to be able to pivot to the open configuration.

Referring to the sequence illustrated in FIGS. 12a and 12b, a user (not shown) manually operates the retaining element 1264 to release the second portion 1202b from the first portion 1202a. The second portion 1202b then pivots about the axis 1268, for example by 45°, out and away from the first portion 1202a, under gravity, by manipulation by a user, by a biasing means (not shown) for biasing the second portion 1202b to pivot out and away from the first portion 1202a, or any combination of these (not shown). A user then places a flavor element 1224 into the second portion 1202b so as to rest on the shelf 1290 of the second portion 1202b (FIG. 12a). A user then pushes or otherwise manipulates the second portion 1202b so that the second portion pivots about the axis 1268 towards the first portion 1202a. In this act the flavor element 1224 is inserted through the opening 1244 of the side wall 1242 of the first portion 1202a and installed in the channel 1232 therein, and the second portion 1202b closes off the opening 1244. As the second portion 1202b is pivoted towards the closed configuration, the latch 1264a of the retaining element 1264 engages with (protrudes into) the notch 1291 of the second portion 1202b, and thereby retains the second portion 1202b relative to the second portion 1202b. The mouth-end section 1202 is thereby in the closed configuration (FIG. 12b).

Figure 13A:
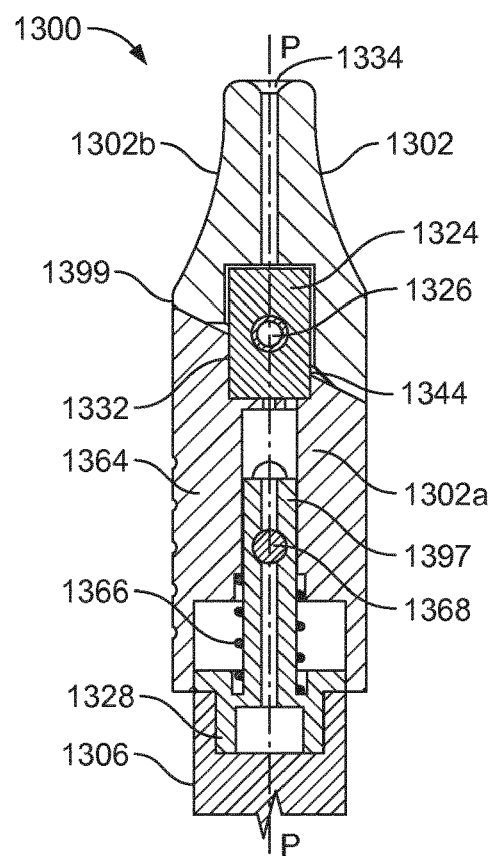
FIGS. 13a to 13c show schematic cross sections of a part of an aerosol provision article comprising a twelfth receptacle section in different configurations according to a twelfth example.
Figure 13B:
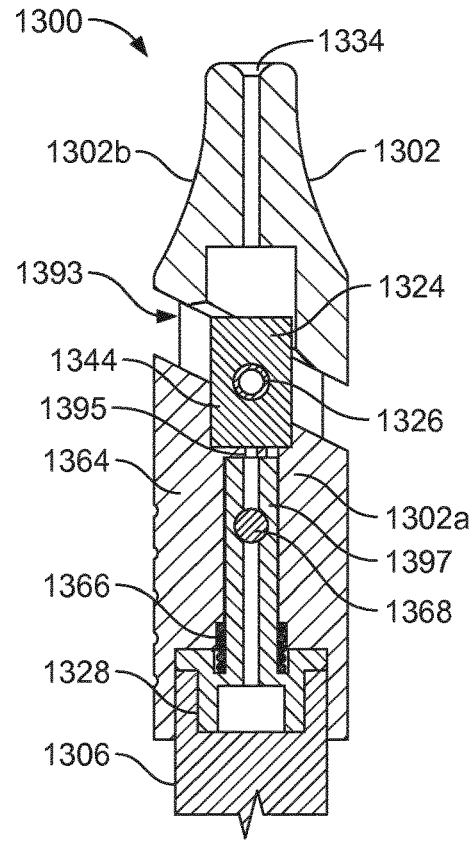
Figure 13C:
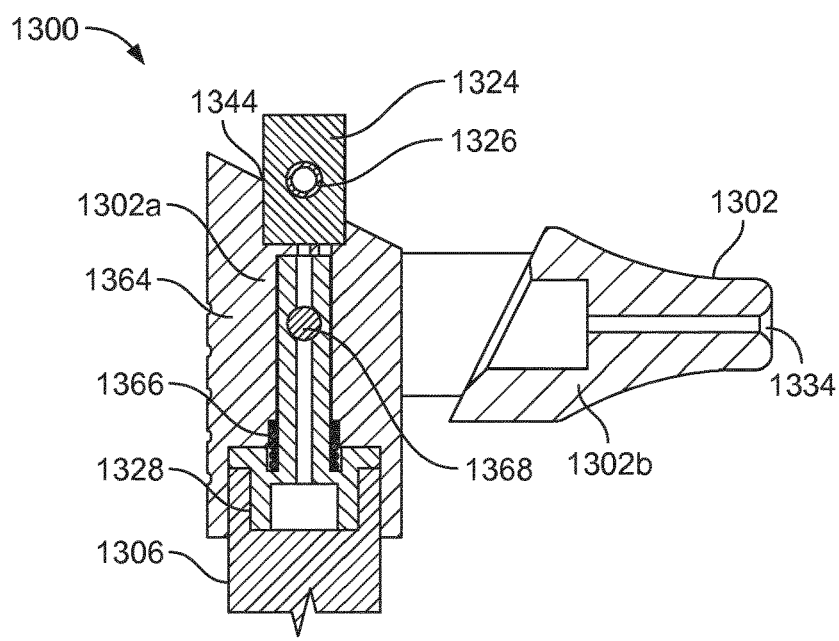

Referring now to FIGS. 13a to 13c, there is illustrated schematically cross sections of a part of an aerosol provision article 1300 with another example receptacle section 1302 in a closed configuration (FIG. 13a) and an open configuration (FIG. 13c). In this example, the receptacle 1302 is again a mouth-end section 1302. For brevity, features in FIG. 13 and the functioning thereof that are the same or similar to those features already described with reference to FIG. 12 are given similar reference numerals to as in FIG. 12 but increased by 100, and will not be described in detail again.

As in the mouth-end section 1202 illustrated in FIGS. 12a and 12b, the mouth-end section 1302 illustrated in FIGS. 13a to 12c comprises a first portion 1302a and a second portion 1302b moveable relative to the first portion 1302a. The second portion 1302b is pivotally mounted 1368 to the first portion 1302a, thereby to allow pivoting of the second portion 1302a relative to the first portion 1302a, about an axis 1368 substantially perpendicular to the longitudinal axis P-P of the mouth-end section, between the closed configuration (FIG. 13a) and the open configuration (FIG. 13c). The second portion 1302b is for receipt in a user's mouth and defines an outlet 1334 for a user to inhale aerosol from the mouth-end section 1302.

In this example, however, a first part 1364 of the first portion 1302a defines an opening 1344 allowing, when the mouth-end section 1302 is in the open configuration, insertion and/or removal of a flavor element 1324 into and/or from a channel 1332 of the first part 1364 of the first portion 1302a, through the opening 1344, in a direction substantially parallel to the longitudinal axis P-P of the mouth-end section 1302. Specifically, when the second portion 1302b is pivoted away from the first portion 1302a (for example so as to make an angle of for example 90° with respect to the longitudinal axis of the mouth-end section 1302), the mouth-end section 1302 is in the open configuration, and the opening 1344 is exposed (FIG. 13b). When the second portion 1302a is pivoted towards the first portion 1302a (for example so as to be co-axial with the first portion 1302a, i.e. make an angle of for example 0° with respect to the longitudinal axis of the mouth-end section 1302), the mouth-end section 1302 is in the closed configuration, and the opening 1344 closed off by the second portion 1302b (FIG. 13a).

The channel 1332 is internal of and extends along the length of the first part 1364 of the first portion 1302a. The first part 1364 of the first portion 1302a comprises a supporting element 1395 that supports the flavor element 1324 received in the opening 1344, and prevents the flavor element 1324 from being received entirely in the channel 1332 of the first part 1364 of the first portion 1302a. The first portion 1302a is thereby arranged such that the flavor element 1324 received in the opening 1344 in use protrudes out from the opening 1344. This enables a user, when the mouth-end section 1302 is in the open configuration (FIG. 13c), to easily manually grasp or otherwise manipulate the flavor element 1324 into and or from the mouth-end section 1302. As with all of the examples, the flavor element may comprise a crushable flavor capsule 1326.

A second elongate part 1397 of the first portion 1302a is arranged in the channel 1332 and comprises a connecting element 1328 for releasably connecting the mouth-end section 1302 to a body 1306 of the overall device 1300. The first part 1364 of the first portion 1302a is slidably mounted with respect to the second part 1397 of the first portion 1302a to enable sliding of the first part 1364, relative to the second part 1397, substantially parallel to the longitudinal axis P-P of the mouth-end section 1302. The first portion 1302a comprises a biasing means, such as a spring 1366, to bias the first part 1364 of the first portion 1302a away from the second part 1397 substantially parallel to the longitudinal axis P-P of the mouth-end section 1302.

The second portion 1302b is pivotally mounted, about an axis 1368 substantially perpendicular to the longitudinal axis P-P of the mouth-end section 1302, to the second part 1397 of the first portion 1302a. The mounting of the second portion 1302b to the second part 1397 of the first portion 1302a is via slots (not visible in the Figures) in opposing sides of the first part 1364 of the first portion 1302a.

The first part 1364 of the first portion 1302a acts as a retaining element 1364 to releasably retain the second portion 1302b in the closed configuration (FIG. 13a). Specifically, the retaining element (i.e. the first part of the first portion) 1364 is slidable, by a user, in use, substantially parallel to the longitudinal axis P-P of the mouth-end section between a first position (FIG. 13a) for obstructing the pivoting of the second portion 1302b about the second part 1397 of the first portion 1302a, and a second position (FIG. 13b) for allowing pivoting of the second portion 1302b about the second part 1397 of the first portion 1302a.

More specifically, when the mouth-end section 1302 is in the closed configuration, an interface 1399 between the retaining element (i.e. the first part of the first portion) 1364 and the second portion 1302*b* is angled with respect to a plane parallel to the longitudinal axis P-P of the mouth-end section 1302, and is angled with respect to a plane substantially perpendicular to the longitudinal axis P-P of the mouth-end section 1302 (see FIG. 13*a*). The angle may be, for example, 45° with respect to both the plane parallel to the longitudinal axis P-P of the mouth-end section 1302 and the plane substantially perpendicular to the longitudinal axis P-P of the mouth-end section 1302. This ensures that when the retaining element 1364 is in the first portion (FIG. 13*a*), pivoting (rotation) of the second portion 1302*b* about the axis 1368 is obstructed by the retaining element 1364, and hence the mouth-end section 1302 is retained in the closed configuration (FIG. 13*a*). The spring 1366 biases the retaining element 1364 to the first portion, hence ensuring the mouth-end section 1302 is retained in the closed configuration in use.

However, when the retaining element 1364 is in the second position (FIG. 13*b*), i.e. slid or otherwise manipulated by a user substantially parallel to the longitudinal axis P-P of the mouth-end section 1302 away from the second portion 1302*b*, a gap 1393 is created between the second portion 1302*b* and the retaining element 1364. The gap 1393 provides sufficient clearance of the retaining element 1364 from the second portion 1302*b* such that the second portion 1302*b* is free to pivot about the axis 1368 (clockwise in the sense of FIGS. 13*a* to 13*c*). This exposes the opening 1344 for a user to insert, remove and/or a replace a flavor flavour element 1324 therein. The mouth-end section 1302 is thereby in the open configuration (FIG. 13*c*).

Referring to the sequence illustrated in FIGS. 13*a* to 13*c*, the mouth-end section 1302 is first in the closed configuration (FIG. 13*a*). A user may pull or otherwise manipulate the retaining element 1364 (first part 1364 of the first portion 1302*a*) substantially parallel to the longitudinal axis P-P of the mouth-end section 1302 away from the second portion 1302*b* (FIG. 13*b*). A user then rotates (clockwise in the sense of FIGS. 13*a* to 13*c*) or otherwise manipulates the second portion 1302*b*, relative to the first portion 1302*a*, about the axis 1368 substantially perpendicular to the longitudinal axis P-P of the mouth-end section 1302. The mouth-end section 1302 is thereby in the open configuration, and the flavor element 1324 received in the opening 1344 is thereby exposed for a user to manually grasp and pull or otherwise manipulate out of the opening 1344 (FIG. 13*c*). A user may then replace the flavor element 1324 into the opening 1344. A user may then rotate (anti-clockwise in the sense of FIGS. 13*a* to 13*c*) or otherwise manipulate the second portion 1302*b*, relative to the first portion, about the axis 1368 substantially perpendicular to the longitudinal axis P-P of the mouth-end section 1302. The mouth-end section 1302 is thereby returned to the closed configuration (as in FIG. 13*a*) and is ready to use.

Although in the examples described above, the element 124, 224, 324 etc. received in the various receptacle sections 202, 302, 402 etc. is a flavor element 124, 224, 324 etc. and is for imparting a flavor to the aerosol when the aerosol flows through the flavor element 124, 224, 324 etc., this is not essential and instead (or in addition) the element 124, 224, 324 etc. may be for modifying a property of the aerosol other than (or in addition) to flavor, for example it could comprise a substance for modifying a property of the aerosol other than (or in addition) to flavor.

In some examples, the element 124, 224, 324 etc. may comprise a substance that modifies one or more other organoleptic properties of the aerosol (e.g. modifying the feel or smell or look of the aerosol to the user).

In some examples, the element 124, 224, 324 etc. may comprise a substance that modifies the PH of the aerosol by either lowering or raising the PH (e.g. modifying the acidity or the basicity of the aerosol).

In some examples, the element 124, 224, 324 etc. may comprise a substance that modifies (e.g. reduce) the amount of aldehydes in the aerosol.

In some examples, the element 124, 324, 324 etc. may comprise a substance that modifies different combinations of two or more of these or indeed other properties of the aerosol.

Although in the above described examples, the device 100, 200, 300, etc., generates the aerosol by heating a liquid (the device is of type commonly referred to as an e-cig), this is not essential and in other examples, the device may generate the aerosol by heating, but not burning (combusting), a material, for example comprising a solid material, that may contain for example tobacco (e.g. a device sometimes referred to as a Tobacco Heating Product (THP) device).

In the above examples, the liquid container 122 was cylindrical in shape and defined a cylindrical channel 104 running through the length of the liquid container 122. However, in other examples, the liquid container may not be annular in shape, and/or the liquid container may comprise an outer shell that defines an annular channel between the liquid container and the outer shell through which vapor or aerosol may also, or instead, pass.

Indeed, it will be readily appreciated that there are many configurations of aerosol provision articles such as so called e-cigarette devices (some of which not having refillable liquid containers integral to the device as such, but rather, for example, replaceable cartridges, for example comprising integral atomizers, i.e. so called "cartomizers") and that the above examples may also be applied to these or other configurations or to other aerosol provision articles.

In use, the liquid may be heated to a temperature of between around 100-300° C. or more particularly around 150° C. to 250° C. Suitable liquid materials 118 include materials that provide volatilized components upon heating, typically in the form of an aerosol. Suitable materials that the flavor element may be or comprise include any tobacco-containing material and may, for example, include one or more of tobacco per se, different varieties of tobacco, tobacco derivatives, pelletized tobacco, extruded tobacco, expanded tobacco, reconstituted tobacco, ground tobacco, tobacco extract, homogenized tobacco or tobacco substitutes. In the case of tobacco, the material may be in the form of a rod of tobacco, a pod or plug of tobacco, loose tobacco, agglomerates, etc., and may be in relatively dry form or in relatively moist form for example. The tobacco may have been modified, for example chemically modified, for example had its pH modified so as to promote the release of selected constituents of the tobacco such as nicotine. Suitable solid materials may include other, non-tobacco, products, which, depending on the product, may or may not contain nicotine. A tobacco rod may be formed using a wrapping material.

As used herein, the terms "flavor" and "flavorant" may refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, pimento, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, solid, or powder. For example, a liquid, oil, or other such fluid flavorant may be impregnated in a porous solid material so as to impart flavor and/or other properties to that porous solid material. As such, the liquid or oil is a constituent of the material in which it is impregnated.

The above embodiments are to be understood as illustrative examples of the disclosure. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A receptacle section for an aerosol provision article, the aerosol provision article for generating a flow of aerosol in use, the receptacle section arranged for receiving therein an element for modifying a property of aerosol passing through said element received in the receptacle section in use, the receptacle section being configurable between a first configuration and a different, second configuration, the first configuration defining a flow path for said aerosol to flow through the receptacle section via said element received in the receptacle section in use, and the second configuration allowing said element to be inserted into and/or removed from the receptacle section, the receptacle section comprising:
   a first portion; and
   a second portion moveable relative to the first portion,
   wherein a movement of the second portion relative to the first portion changes configuration of the receptacle section between the first configuration and the second configuration, and wherein the movement comprises movement substantially parallel to a longitudinal axis of the receptacle section;
   wherein the second portion is slidably mounted to the first portion thereby to allow sliding of the second portion relative to the first portion, parallel to the longitudinal axis of the receptacle section, between the first configuration and the second configuration; and
   wherein the receptacle section is arranged to allow at least one of insertion or removal of the element into or from the receptacle section in a direction substantially perpendicular to the longitudinal axis of the receptacle section.

2. A receptacle section for an aerosol provision article, the aerosol provision article for generating a flow of aerosol in use, the receptacle section arranged for receiving therein an element for modifying a property of aerosol passing through said element received in the receptacle section in use, the receptacle section being configurable between a first configuration and a different, second configuration, the first configuration defining a flow path for said aerosol to flow through the receptacle section via said element received in the receptacle section in use, and the second configuration allowing said element to be inserted into and/or removed from the receptacle section, the receptacle section comprising:
   a first portion; and
   a second portion moveable relative to the first portion,
   wherein a movement of the second portion relative to the first portion changes configuration of the receptacle section between the first configuration and the second configuration, and wherein the movement comprises movement substantially parallel to a longitudinal axis of the receptacle section;
   wherein the second portion is slidably mounted to the first portion thereby to allow sliding of the second portion relative to the first portion, parallel to the longitudinal axis of the receptacle section, between the first configuration and the second configuration;
   wherein the receptacle section is arranged to allow, when in the second configuration, at least one of insertion or removal of the element into or from the receptacle section in a direction substantially perpendicular to the longitudinal axis of the receptacle section; and
   wherein the receptacle section is arranged to allow the insertion or removal of the element through an opening of the second portion, the opening being for outlet of the aerosol flowing through the receptacle section in use for inhalation by a user.

3. The receptacle section according to claim 2, wherein the receptacle section comprises, at the opening, a lip portion for retaining the element in the receptacle section in use.

4. The receptacle section according to claim 2, wherein movement of the second portion towards the first portion causes the element when inserted in the receptacle section to protrude out of the opening.

5. The receptacle section according to claim 4, wherein the receptacle section comprises, at the opening, a lip portion, and the lip portion is arranged to cause the element to remain protruded out of the opening on a subsequent movement of the second portion away from the first portion.

6. The receptacle section according to claim 2, wherein the receptacle section is biased to the first configuration.

7. The receptacle section according to claim 1, wherein the second portion is receivable in the first portion, and a side wall of the second portion defines an opening, wherein in the second configuration the opening is exposed for insertion or removal of the element into the second portion through the opening, and wherein in the first configuration the opening is closed off by the first portion.

8. The receptacle section according to claim 7, wherein the receptacle section comprises a third portion for closing off the opening, the third portion being pivotally mounted to the second portion, thereby to allow pivoting of the third portion relative to the second portion, wherein in the second configuration the third portion is exposed out of the first portion thereby to allow the pivoting of the third portion, and wherein in the first configuration the third portion is received in the first portion.

9. The receptacle section according to claim 1, wherein the first portion is receivable in the second portion, and a side wall of the first portion defines an opening, wherein in the second configuration the opening is exposed for insertion or removal of the element into the first portion through the opening, and wherein in the closed configuration the opening is closed off by the second portion.

10. The receptacle section according to claim 1, wherein the first portion comprises a retaining element to releasably retain the second portion relative to the first portion such that the receptacle section is in the first configuration.

11. The receptacle section according to claim 10, wherein the receptacle section is biased towards the second configuration.

12. A receptacle section for an aerosol provision article, the aerosol provision article for generating a flow of aerosol in use, the receptacle section arranged for receiving therein an element for modifying a property of aerosol passing through said element received in the receptacle section in use, the receptacle section being configurable between a first configuration and a different, second configuration, the first configuration defining a flow path for said aerosol to flow through the receptacle section via said element received in the receptacle section in use, and the second configuration allowing said element to be inserted into and/or removed from the receptacle section, the receptacle section comprising:
    a first portion; and
    a second portion moveable relative to the first portion, wherein a movement of the second portion relative to the first portion changes configuration of the receptacle section between the first configuration and the second configuration, and wherein the movement comprises movement substantially parallel to a longitudinal axis of the receptacle section;
    wherein the second portion is slidably mounted to the first portion thereby to allow sliding of the second portion relative to the first portion, parallel to the longitudinal axis of the receptacle section, between the first configuration and the second configuration;
    wherein the receptacle section is arranged to allow, when in the second configuration, at least one of insertion or removal of the element into or from the receptacle section in a direction substantially perpendicular to the longitudinal axis of the receptacle section;
    wherein the second portion is removable from the first portion, wherein the receptacle section is in the second configuration when the second portion is removed from the first portion, and the receptacle section is in the first configuration when the second portion is connected to the first portion; and
    wherein at least the first portion or the second portion comprises a receiving portion for allowing, when the second portion is removed, insertion or removal of the element into or from the receiving portion in a direction substantially perpendicular to the longitudinal axis of the receptacle section.

13. The receptacle section according to claim 12, wherein the receiving portion is either:
    receivable in the first portion, or
    defines an aperture into which the element can be inserted to be supported by the receiving portion.

14. The receptacle section according to claim 1, wherein either:
    at least a portion of the second portion is for receipt into a user's mouth, or
    the first portion comprises a connecting portion for releasably connecting the receptacle section to the aerosol provision article.

15. The receptacle section according to claim 1, the receptacle section having the element received therein.

16. The receptacle according to claim 15, wherein either:
    the property is one or more of an organoleptic property of the aerosol, a flavor of the aerosol, and the pH of the aerosol, or
    the element is self-supporting or is or comprises tobacco or a crushable flavor capsule for releasing, when crushed, a flavorant into the flow of aerosol.

17. A mouthpiece for an aerosol provision article, the aerosol provision article being for generating a flow of aerosol in use, the mouthpiece comprising the receptacle section of claim 1.

18. An aerosol provision article for generating a flow of aerosol in use, the aerosol provision article comprising the receptacle section of claim 1.

19. The aerosol provision article according to claim 18, comprising:
    a container for holding a liquid or a material; and
    a heater for volatilizing liquid held in the container to generate the flow of aerosol in use or for heating but not combusting the material to generate the flow of aerosol in use.

* * * * *